(12) United States Patent
Chen

(10) Patent No.: US 6,828,121 B2
(45) Date of Patent: Dec. 7, 2004

(54) BACTERIAL HOST STRAINS

(75) Inventor: Christina Yu-Ching Chen, Hillsborough, CA (US)

(73) Assignee: Genentech, Inc., South San Francisco, CA (US)

(*) Notice: Subject to any disclaimer, the term of this patent is extended or adjusted under 35 U.S.C. 154(b) by 213 days.

(21) Appl. No.: 10/011,125

(22) Filed: Dec. 7, 2001

(65) Prior Publication Data

US 2002/0142388 A1 Oct. 3, 2002

Related U.S. Application Data

(60) Provisional application No. 60/256,162, filed on Dec. 14, 2000.

(51) Int. Cl.$^7$ .......................... C12P 21/06; C12P 21/04; C12N 1/20
(52) U.S. Cl. .................. 435/69.1; 435/69.6; 435/71.1; 435/71.2; 435/252.33
(58) Field of Search ............................... 435/69.1, 69.6, 435/71.1, 71.2, 252.33

(56) References Cited

U.S. PATENT DOCUMENTS

| | | | |
|---|---|---|---|
| 4,439,523 A | * | 3/1984 | Malick et al. |
| 4,816,567 A | | 3/1989 | Cabilly et al. |
| 5,508,192 A | | 4/1996 | Georgiou et al. |
| 6,251,395 B1 | * | 6/2001 | Gallatin et al. |

FOREIGN PATENT DOCUMENTS

| | | |
|---|---|---|
| EP | 0731167 A1 | 11/1996 |
| WO | WO 88/05821 | 8/1988 |
| WO | WO 93/07896 | 4/1993 |
| WO | WO 00/39309 | 7/2000 |

OTHER PUBLICATIONS

Duenas et al (Gene vol. 158(1) pp 61–66), May 26, 1995.*
Baneyx and Georgiou, "Construction and characterization of *Escherichia coli* strains deficient in multiple secreted proteases: protease III degrades high–molecular–weight substrates in vivo" *J. Bacteriol.* 173 (8) :2696–2703 (1991).
Baneyx and Georgiou, "Degradation of Secreted Proteins in *Escherichia coli*"*Annals of New York Acad. Sci.* 665: 301–308 (1992).
Boss et al., "Assembly of functional antibodies from immunoglobulin heavy and light chains synthesised in E. coli" *Nucleic Acids Research* 12 (9) :3791–3806 (1984).
Cabilly et al., "Generation of antibody activity from immunoglobulin polypeptide chains produced in *Escherichia coli*" *Proc. natl. Acad. Sci. USA* 81: 3273–3277 (1984).
Cavard et al., "The acylated precursor form of the colicin A lysis protein is a natural substrate oft he DegP protease" *J. Bacteriol.* 171(11): 6316–6322 (1989).
Gottesman, S., "Proteases and their targets in *Escherichia coli*" *Annu. Rev. Gent.* 30: 465–506 (1996).

Keiler and Sauer, "Identification of acive site residues of the Tsp protease" *Journal of Biological Chemistry* 270 (48) : 28864–28868 (1995).
Meerman and Georgiou, "Construction and characterization of a set of *E. coli* strains deficient in all known loci affecting the proteolytic stability of secreted recombinant proteins" *Bio/Technology* 12:1107–1110 (1994).
Pluckthun, A., "Mono– and bivalent antibody fragments produced in *Escherichia coli*: engineering, folding and antigen binding" *Immunol. Revs.* 130: 151–188 (1992).
Skerra, A., "Bacterial expression of immunoglobulin fragments" *Curr. Opinion in Immunol.* 5:256–262 (1993).
Spiess et al., "A temperature–dependent switch from chaperone to protease in a widely conserved heat shock protein" *Cell* 97: 339–347. (1999).
Strauch et al., "Characterization of degP, a gene required for proteolysis in the cell envelope and essential for growth of *Escherichia coli* at high temperature" *J. Bacteriol.* 171(5) :2690–2696 (1989).
Baneyx and Georgiou., "Expression of Proteolytically Sensitive Polypeptides in *Escherichia coli.*" *Stability of Protein Pharmaceuticals.*, Ahern and Manning, eds., NY:Plenum Press, Chapter 3, pp. 69–108 (1992).
Bass et al., "Multicopy Suppressors of Prc Mutant *Escherichia coli* Include Two HtrA (DegP) Protease Homologs (HhoAB), DksA, and a Truncated RlpA." *J. Bacteriol.* 178(4) : 1154–1161 (1996).
Black et al., "A Promoter Associated with the Neisserial Repeat Can Be Used To Transcribe the uvrB Gene from *Neisseria gonorrhoeae.*" *J. Bacteriol.* 177 (8) : 1952–1958 (1995).
Brand et al., "Cloning and Sequencing of the petBD Operon from the *Cyanobacterium synechococcus* sp. PCC 7002" *Plant Mol. Bio.* 20: 481–491 (1992).
Chaudhury and Smith., "*Escherichia coli* recBC Deletion Mutants." *J. Bacteriol.* 160 (2): 788–791 (Nov. 1984).
Elish et al., "Biochemical Analysis of Spontaneous fepA Mutants of *Escherichia coli.*" *J. Gen. Microbiol.* 134: 1355–1364 (1988).
Fleischmann et al., "Whole–Genome Random Sequencing and Assembly of *Haemophilus influenzae* Rd." *Science.* 269: 496–512 (Jul. 28, 1995).
Hara et al., "Cloning, Mapping, and Characterization of the *Escherichia coli* prc Gene, Which is Involved in C–Terminal Processing of Penicillin–Binding Protein 3." *J. Bacteriol.* 173 (15) : 4799–4813 (Aug. 1991).

(List continued on next page.)

*Primary Examiner*—Mark Navarro
(74) *Attorney, Agent, or Firm*—Janet E. Hasak

(57) ABSTRACT

An *E. coli* strain is described that is deficient in chromosomal degP and prc encoding protease DegP and Prc, respectively, and harbors a mutant spr gene that encodes a protein that suppresses growth phenotypes exhibited by strains harboring prc mutants. Preferably, the strain comprises nucleic acid encoding a polypeptide heterologous to the strain, so that a heterologous polypeptide can be produced therefrom.

24 Claims, 18 Drawing Sheets

OTHER PUBLICATIONS

Hara et al., "*E. coli* PBP 7 is a Multicopy Suppressor of a Defect Due to the Lack of Spr which is Likely To Be Also a Peptidoglycan–Hydrolyzing Enzyme." *Abstract for Table Ronde Roussel Uclat No. 86* (Versailles) (May 1997).

Hara et at., "Overproduction of Penicillin–Binding Protein 7 Suppresses Thermosensitive Growth Defect at Low Osmolarity Due to an spr Mutation of *Escherichia coli.*" *Micro. Drug Resistance*, 2 (1) :63–72 (1996).

Keiler et al., "C–Terminal Specific Protein Degradation: Activity and Substrate Specificity of the Tsp Protease." *Protein Science*. 4: 1507–1515 (1995).

Kim et al., "Selective Degradation of Unfolded Proteins by the Self–Compartmentalizing HtrA Protease, A Periplasmic Heat Shock Protein in *Escherichia coli.*" *J. Mol. Biol.* 294: 1363–1374 (1999).

Mitchell and Minnick., "A Carboxy–Terminal Processing Protease Gene is Located Immediately Upstream of the Invasion–Associated Locus from *Bartonella bacilliformis.*" *Microbiol.* 143: 1221–1233 (1997).

Park et al., "Secretory Production of Recombinant Protein by a High Cell Density Culture of a Protease Negative Mutant *Escherichia coli* Strain." *Biotechnol. Prog.* 15: 164–167 (1999).

Shestakov et al., "Molecular Cloning and Characterization of the ctpA Gene Encoding a Carboxyl–Terminal Processing Protease." *J. Bio. Chem.* 269 (30) : 19354–19359 (Jul. 1994).

Silber et al., "Tsp: A Tail–Specific Protease that Selectively Degrades Proteins with Nonpolar C Termini." *Proc. Natl. Acad. Sci. USA* 89: 295–299 (Jan. 1992).

Skorko–Glonek et al., "Site–Directed Mutagenesis of the HtrA (DegP) Serine Protease, Whose Proteolytic Activity is Indispensable for *Escherichia coli* Survival at Elevated Temperatures." *Gene* 163: 47–52 (1995).

Strauch and Beckwith., "An *Escherichia coli* Mutation Preventing Degradation of Abnormal Periplasmic Proteins." *Proc. Natl. Acad. Sci. USA* 85: 1576–1580 (Mar. 1988).

\* cited by examiner

```
  1 GAATTCAACT TCTCCATACT TTGGATAAGG AAATACAGAC ATGAAAAATC TCATTGCTGA

61 GTTGTTATTT AAGCTTTGGA GATTATCGTC ACTGCAATGC TTCGCAATAT GGCGCAAAAT

121 GACCAACAGC GGTTGATTGA TCAGGTAGAG GGGGCGCTGT ACGAGGTAAA GCCCGATGCC

181 AGCATTCCTG ACGACGATAC GGAGCTGCTG CGCGATTACG TAAAGAAGTT ATTGAAGCAT

241 CCTCGTCAGT AAAAAGTTAA TCTTTTCAAC AGCTGTCATA AAGTTGTCAC GGCCGAGACT

301 TATAGTCGCT TTGTTTTTAT TTTTTAATGT ATTTGTAACT AGAATTCGAG CTCGGTACCC

341 GGGGATCCTC TAGAGGTTGA GGTGATTTT   ATG AAA AAG AAT ATC GCA TTT CTT
-23                                  M   K   K   N   I   A   F   L
```

FIGURE 1A

```
414 CTT GCA TCT ATG TTC GTT TTT TCT ATT GCT ACA AAC GCG TAC GCT GAT ATC
-15  L   A   S   M   F   V   F   S   I   A   T   N   A   Y   A   D   I

465 CAG TTG ACC CAG TCC CCG AGC TCC CTG TCC GCC TCT GTG GGC GAT AGG GTC
  2  Q   L   T   Q   S   P   S   S   L   S   A   S   V   G   D   R   V

516 ACC ATC ACC TGC AGC GCA AGT CAG GAT ATT AGC AAC TAT TTA AAC TGG TAT
 19  T   I   T   C   S   A   S   Q   D   I   S   N   Y   L   N   W   Y

567 CAA CAG AAA CCA GGA AAA GCT CCG AAA GTA CTG ATT TAC TTC ACC TCC TCT
 36  Q   Q   K   P   G   K   A   P   K   V   L   I   Y   F   T   S   S

618 CTC CAC TCT GGA GTC CCT TCT CGC TTC TCT GGA TCC GGT TCT GGG ACG GAT
 53  L   H   S   G   V   P   S   R   F   S   G   S   G   S   G   T   D

669 TTC ACT CTG ACC ATC AGC AGT CTG CAG CCA GAA GAC TTC GCA ACT TAT TAC
 70  F   T   L   T   I   S   S   L   Q   P   E   D   F   A   T   Y   Y

720 TGT CAA CAG TAT AGC ACC GTG CCG TGG ACG TTT GGA CAG GGT ACC AAG GTG
 87  C   Q   Q   Y   S   T   V   P   W   T   F   G   Q   G   T   K   V
```

FIGURE 1B

```
 771 GAG ATC AAA CGA ACT GTG GCT GCA CCA TCT GTC TTC ATC TTC CCG CCA TCT
 104 E   I   K   R   T   V   A   A   P   S   V   F   I   F   P   P   S

822 GAT GAG CAG TTG AAA TCT GGA ACT GCT TCT GTT GTG TGC CTG CTG AAT AAC
 121 D   E   Q   L   K   S   G   T   A   S   V   V   C   L   L   N   N

873 TTC TAT CCC AGA GAG GCC AAA GTA CAG TGG AAG GTG GAT AAC GCC CTC CAA
 138 F   Y   P   R   E   A   K   V   Q   W   K   V   D   N   A   L   Q

924 TCG GGT AAC TCC CAG GAG AGT GTC ACA GAG CAG GAC AGC AAG GAC AGC ACC
 155 S   G   N   S   Q   E   S   V   T   E   Q   D   S   K   D   S   T

975 TAC AGC CTC AGC AGC ACC CTG ACG CTG AGC AAA GCA GAC TAC GAG AAA CAC
 172 Y   S   L   S   S   T   L   T   L   S   K   A   D   Y   E   K   H

1026 AAA GTC TAC GCC TGC GAA GTC ACC CAT CAG GGC CTG AGC TCG CCC GTC ACA
 189 K   V   Y   A   C   E   V   T   H   Q   G   L   S   S   P   V   T

1077 AAG AGC TTC AAC AGG GGA GAG TGT TAA GCTGATC CTCTACGCCG
 206 K   S   F   N   R   G   E   C

1121 GACGCATCGT GGCCCTAGTA CGCAACTAGT CGTAAAAAGG GTATCTAGAG GTTGAGGTGA
```

FIGURE 1C

```
1181 TTTT    ATG AAA AAG AAT ATC GCA TTT CTT CTT GCA TCT ATG TTC GTT
 -23         M   K   K   N   I   A   F   L   L   A   S   M   F   V

1227 TTT TCT ATT GCT ACA AAC GCG TAC GCT GAG GTT CAG CTG GTG GAG TCT
  -9 F   S   I   A   T   N   A   Y   A   E   V   Q   L   V   E   S

1275 GGC GGT GGC CTG GTG CAG CCA GGG GGC TCA CTC CGT TTG TCC TGT GCA
   8 G   G   G   L   V   Q   P   G   G   S   L   R   L   S   C   A

1323 GCT TCT GGC TAC GAC TTC ACG CAC TAC GGT ATG AAC TGG GTC CGT CAG
  24 A   S   G   Y   D   F   T   H   Y   G   M   N   W   V   R   Q

1371 GCC CCG GGT AAG GGC CTG GAA TGG GTT GGA TGG ATT AAC ACC TAT ACC
  40 A   P   G   K   G   L   E   W   V   G   W   I   N   T   Y   T

1419 GGT GAA CCG ACT TAT GCT GCG GAT TTC AAA CGT CGT TTC ACT TTT TCT
  56 G   E   P   T   Y   A   A   D   F   K   R   R   F   T   F   S

1467 TTA GAC ACC TCC AAA AGC ACA GCA TAC CTG CAG ATG AAC AGC CTG CGC
  72 L   D   T   S   K   S   T   A   Y   L   Q   M   N   S   L   R

1515 GCT GAG GAC ACT GCC GTC TAT TAC TGT GCA AAG TAC CCG TAC TAT TAT
  88 A   E   D   T   A   V   Y   Y   C   A   K   Y   P   Y   Y   Y

1563 GGC ACG AGC CAC TGG TAT TTC GAC GTC TGG GGT CAA GGA ACC CTG GTC
 104 G   T   S   H   W   Y   F   D   V   W   G   Q   G   T   L   V
```

FIGURE 1D

```
1611 ACC GTC TCC TCG GCC TCC ACC AAG GGC CCA TCG GTC TTC CCC CTG GCA
 120 T   V   S   S   A   S   T   K   G   P   S   V   F   P   L   A

1659 CCC TCC TCC AAG AGC ACC TCT GGG GGC ACA GCG GCC CTG GGC TGC CTG
 136 P   S   S   K   S   T   S   G   G   T   A   A   L   G   C   L

1707 GTC AAG GAC TAC TTC CCC GAA CCG GTG ACG GTG TCG TGG AAC TCA GGC
 152 V   K   D   Y   F   P   E   P   V   T   V   S   W   N   S   G

1755 GCC CTG ACC AGC GGC GTG CAC ACC TTC CCG GCT GTC CTA CAG TCC TCA
 168 A   L   T   S   G   V   H   T   F   P   A   V   L   Q   S   S

1803 GGA CTC TAC TCC CTC AGC AGC GTG GTG ACC GTG CCC TCC AGC AGC TTG
 184 G   L   Y   S   L   S   S   V   V   T   V   P   S   S   S   L

1851 GGC ACC CAG ACC TAC ATC TGC AAC GTG AAT CAC AAG CCC AGC AAC ACC
 200 G   T   Q   T   Y   I   C   N   V   N   H   K   P   S   N   T

1899 AAG GTC GAC AAG AAA GTT GAG CCC AAA TCT TGT GAC AAA ACT CAC CTC
 216 K   V   D   K   K   V   E   P   K   S   C   D   K   T   H   L

1947 TAG AA
```

FIGURE 1E

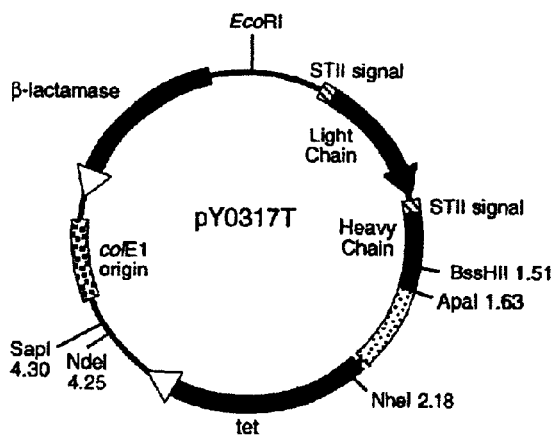
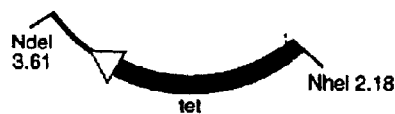
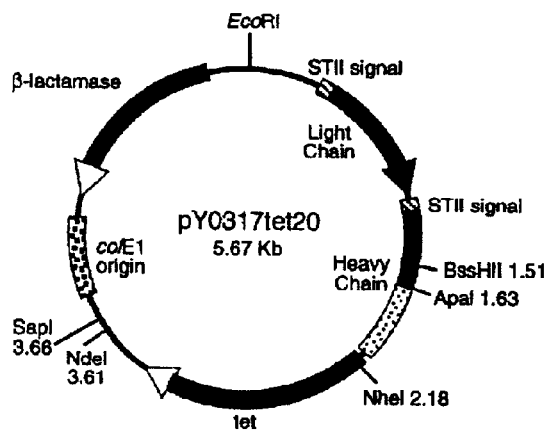
FIGURE 2B

```
  1  TTTCCTCACTGACTATAAAGAATAGAGAAGGAAGGGCTTCAGTGACCGGCTGCCTGGCTGACTTACAGCAGTCAGACTCTGACAGGATC

1  ATGGCTATGATGGAGGTCCAGGGGGACCAGGGGACCTGGGACCAGCCTGGGCCTGCTGCCGTGCTGATCGTGATCTTCACAGTGCTCCTGCAGTCTCTGT
  1  MetAlaMetMetGluValGlnGlyProSerLeuGlyGlyProSerLeuGlyGlnThrCysValLeuIleValIlePheThrValLeuGlnSerLeuCys

181  GTGGCTGTAACTTACTTACGTGTACTTACCAACGAGCTGAAGCAGATGCAGGACAAGTACTCCAAAAGTGGCATTGCTTGTTCTTAAAAGAA
 31  ValAlaValThrTyrTyrValTyrPheThrAsnGluLeuLysGlnMetGlnAspLysTyrSerGlyIleAlaCysPheLeuLysGlu

271  GATGACAGTTATTGGGACCCCAATGACGAAGAGAGTATGAACAGCCCCTGCTGGCAAGTGGCAACTCCGTCAGCTCGTTAGAAAG
 61  AspAspSerTyrTrpAspProAsnAspGluGluSerMetAsnSerProCysTrpGlnValLysTrpGlnLeuArgGlnLeuValArgLys

361  ATGATTTTGAGAACCTCTGAGGAACCATTCTACAGTTCAAGAAAAGCAACAAAATATTTCTCCCTAGTGAGAGAAAGAGGTCCNCAG
 91  MetIleLeuArgThrSerGluGluProIleLeuGlnPheLysLysSerAsnLysIlePheSerProLeuValArgGluArgGlyProGln
                                                                                          *

451  AGAGTAGCAGCTCACATAACTGGGACCAGAGAAGCAACACATTGTCTCTTCCAAACTCCAAGAATGAAAAGGCTCTGGGCCGCAAA
121  ArgValAlaAlaHisIleThrGlyThrArgGlyArgSerArgAsnThrLeuSerSerProAsnSerLysAlaLeuGlyArgLys

541  ATAAACTCCTGGGAATCATCAAGGAGTGGGCATTCATTCCTGAGCCACTTGAGGAATGGTGAACTGGTCATCCATGAAAAAGGG
151  IleAsnSerTrpGluSerSerArgSerGlyHisSerPheLeuSerAsnLeuArgAsnGlyGluValIleHisGluLysGly

631  TTTTACTACATCTATTCCCAAACATATCTTTCGATTTCAGAGGGAAATAAAGAAAAACACAAGAACGACAAACAAATGGTTCCAATATATT
181  PheTyrTyrIleTyrSerGlnThrTyrPheArgPheGlnGluIleLysGluAsnThrLysGluAsnAspLysGlnMetValGlnTyrIle

721  TACAAATACAACAAGTTATCCGACCTATATTGTTGATGAAAAGTGCTAGAAAAGTCTAAAGATGCAGAATATGGACTCTAT
211  TyrLysTyrAsnAsnSerTyrProAspProIleLeuLeuMetLysSerAlaArgAsnSerCysTrpSerLysAspAlaGluTyrGlyLeuTyr

811  TCCATCTATCAAGGGGAATATTTGAGCTTAAGGAAATGACAGAATTTTGTTTCTGTAACAAATGACACTTGATAGACATGGACCAT
241  SerIleTyrGlnGlyGlyIleLeuPheGluLeuLysGluLysGluAsnAspArgIleLeuPheValSerValThrAsnGluHisLeuIleAspMetAspHis

901  GAAGCCAGTTTTTTCGGGCCTTTTTAGTTGGCTAACTGACCTGGAAAGAAAAAGCAATAACCTCAAAGTGACTATTCAGTTTTCAGGAT
271  GluAlaSerPhePheGlyAlaPheLeuValGlyStp

991  GATACACTATGAAGATGTTTCAAAAAATCTGACCAAAACAAACAAACAGAAA
```

FIGURE 4

DIQMTQSPSSLSASVGDRVTITCRASQDINNYLNWYQQKPGKAPKLLIYYTSHS
GVPSRFSGSGSGTDYTLTISSLQPEDFATYYCQQGNTLPPTFGQGTKVEIKRT
V/AAPS/V/FIFPPSDEQLKSGTA/S/VV/CLLNNFYPREA/KV/QWKV/DNA/LQSG
9.14    9.14                  8.54 8.54             8.36 8.87   9.17   8.86
NSQESV/TEQDS/KDSTYSLSSTLTLSKA/DYEKHKV/YACEV/THQGLSSPV/
8.35 5.97 7.25 7.4 6.48 6.72
TKSF NRGEC

FIGURE 10

BACTERIAL HOST STRAINS

This application is a non-provisional application filed under 37 CFR 1.53(b) (1), claiming priority under 35 USC 119(e) to provisional application number 60/256,162 filed Dec. 14, 2000, the contents of which are incorporated herein by reference.

BACKGROUND OF THE INVENTION

1. Field of the Invention

The invention relates to using proteolytically-deficient bacterial host strains. More particularly, the invention relates to such host strains that eliminate heterologous polypeptide degradation and improve yield of such polypeptides.

2. Description of Related Art

E. coli strains deficient in proteases or genes controlling the regulation of proteases are known. See, for example, Beckwith and Strauch, WO 88/05821 published Aug. 11, 1988; Chaudhury and Smith, J. Bacteriol., 160: 788–791 (1984); Elish et al., J. Gen. Microbiol., 134: 1355–1364 (1988); Baneyx and Georgiou, "Expression of proteolytically sensitive polypeptides in Escherichia coli," In: Stability of Protein Pharmaceuticals, Vol. 3: Chemical and Physical Pathways of Protein Degradation, Ahem and Manning, eds. (Plenum Press, New York, 1992), p. 69–108.

Some of these strains have been used in attempts to produce efficiently proteolytically sensitive proteins, particularly those of potential medical or commercial importance. U.S. Pat. No. 5,508,192 (to Georgiou et al.) describes the construction of many protease-deficient and/or heat-shock protein-deficient bacterial hosts. Such hosts include single-, double-, triple-, or quadruple-protease-deficient bacteria and single-protease bacteria that also carry a mutation in the rpoH gene. Examples of the protease-deficient strains disclosed include those omitting degP, ompT, ptr3, and/or prc (tsp), and a degP rpoH strain reported to produce large titers of recombinant proteins in E. coli. Park et al., Biotechnol. Prog., 15: 164–167 (1999) also reported that a strain (HM114) deficient in two cell-envelope proteases (degP, prc) grew slightly faster and produced more fusion protein than the other strains deficient in more proteases. They claimed that this strain grew to a cell dry weight of 47.86 g/L in 29 hours using pH-stat, fed-batch cultivation. The protein produced was protein A-β-lactamase fusion protein, which gave 30% higher β-lactamase activity than that obtained from its parent strain KS272.

The Prc protein was first isolated by Ham et al., J. Bacteriol 173: 4799–4813 (1991) as the periplasmic protease that cleaves the carboxyl-terminus of periplasmic penicillin binding protein 3 (PBP3). Subsequently, it was also identified as a protease that selectively degrades proteins with a non-polar C-terminus and was re-named Tsp (Silber et al., Proc. Natl. Acad. Sci. USA, 89: 295–299 (1992)). The prc gene was shown to encode a 75-kDa protein, which is required for protection of cells from combined thermal and osmotic stress (Hara et al., supra). It has been confirmed that the C-terminal sequences determine the substrate preference (Keiler et al., Protein Sci., 4: 1507–1515 (1995)). The amount of cleavage is sensitive to the identity of residues or functional groups at the C-terminus of the substrate protein. The presence of a free α-carboxyl group is important in determining whether closely related peptides with non-polar C-terminal sequences are cleaved efficiently by Prc.

Prc homologs have been identified in a divergent group of prokaryotes, including several cyanobacteria (Brand et al., Plant Mol. Bio., 20: 481–491 (1992); Shestakov et al., J. Biol. Chem., 269: 19354–19359 (1994)), Neisseria gonorrhoeae (Black et al., J. Bacteriol., 177: 1952–1958 (1995)), Haemophilus influenzae (Fleischmann et al., Science, 269: 496–512 (1995)), and Bartonella bacilliformis (GenBank accession no. L37094). A domain in the Prc family of proteins is similar to a domain in the retinol-binding proteins, indicating a common folding domain that may form a binding pocket in these proteins for hydrophobic substrates (Silber et al., supra; Shestakov et al., supra).

Hara et al., supra, discovered that the thermoresistant revertants of Δprc mutants contain extragenic suppressor (spr) mutations. They further identified the wild-type spr gene product to be a lipoprotein in the envelope fraction. They suspected that the wild-type spr gene could be a peptidoglycan-hydrolyzing enzyme (Hara et al, Microbial Drug Resistance, 2: 63–72 (1996)). When the spr is not functional in a prc-plus background, a suppressor for spr mutation was identified to be PBP7, another penicillin-binding protein (Hara et al., 1996, supra). The cloning of spr and the preparation of a Δprc mutant in which Spr is not degraded by the protease are also described in Hara et al., Abstract for Table Ronde Roussel Uclat no. 86, Versailles, May 1997, where the authors concluded that prc and spr are mutual suppressors.

Three multicopy prc suppressors have also been isolated using the conditional lethal phenotype of a prc (tsp) null strain of E. coli (Bass et al., J. Bacteriol., 178: 1154–1161 (1996)). None of them relate to the spr gene. One set of these suppressors is two putative protease genes in tandem that map to 72.5 min on the chromosome. These two genes are htrA homologs, which encode proteins that are 58 and 35% identical, respectively, to the HtrA (DegP) serine protease. Another type of suppressor identified is the dksA (dnak suppressor) gene, which is also a multicopy suppressor of defects in the heat-shock genes dank, dnaj and grpE. The dksA gene was also independently isolated as a multicopy suppressor of a mukB mutation, which is required for chromosomal partitioning. The third type is a truncated lipoprotein A (rlpA) gene.

The gene degP appears to control synthesis of a cell-envelope protease DegP (HtrA). A degP-deficient mutant was first constructed and recombined into an E. coli chromosome by Beckwith and Strauch, supra. HtrA has a high molecular mass of about 500 kDa, which is a heat-shock protein whose proteolytic activity is essential for the survival of E. coli at high temperatures such as above 42° C. (Skorko-Glonek et al., Gene, 163: 47–52 (1995)). A number of ordinarily unstable cell-envelope proteins can be stabilized by the degP mutation (Strauch and Beckwith, Proc. Natl. Acad. Sci. USA, 85: 1676–1580 (1988)). Recently, HtrA protein was reported to behave as a dodecamer consisting of two stacks of hexameric rings by electron microscopy and chemical cross-linking analysis (Kim et al., J. Mol. Biol., 294: 1363–1374 (1999)). Unfolding of protein substrates, such as by exposure to high temperature or reduction of disulfide bonds, is essential for their access into the inner chamber of the double ring-shaped HtrA, where cleavage of peptide bonds may occur (Kim et al., supra).

Many heterologous polypeptides have been produced in various strains deficient in proteases.

However, many of the strains gave relatively low product titer and/or poor growth. There is a need to provide a bacterial strain deficient in proteases that does not result in clipping of the product and provides high product titer.

SUMMARY OF THE INVENTION

Accordingly, the present invention is as claimed. In one aspect the present invention provides E. coli strains that are deficient in chromosomal degP and prc encoding protease DegP and Prc, respectively, and harbor or comprise a mutant spr gene the product of which gene suppresses growth phenotypes exhibited by strains harboring prc mutants. Preferably the strain is not deficient in chromosomal ptr3 encoding Protease III and/or in chromosomal ompT encoding protease OmpT. Preferably, the *E. coli* strain is engineered by introducing the mutant spr gene to a degPΔ prcΔ strain for survival in the stationery phase of a high-cell density *E. coli* fermentation process.

In another embodiment, the strain comprises nucleic acid encoding a polypeptide heterologous to the strain, preferably a proteolytically-sensitive polypeptide, and more preferably a eukaryotic polypeptide.

In a further embodiment, the invention provides a method for producing a heterologous polypeptide, i.e., one that is heterologous to the strain. This method comprises first culturing an *E. coli* strain that is deficient in chromosomal prc encoding protease Prc and harbors or comprises a mutant spr gene the product of which gene suppresses growth phenotypes exhibited by strains harboring prc mutants. This strain also comprises nucleic acid encoding the heterologous polypeptide. The culturing is such that the nucleic acid is expressed. In a second step of this method, the polypeptide is recovered from the strain, whether from the cytoplasm, periplasm, or culture medium, preferably the periplasm or culture medium, and most preferably from fermentation whole broth. Preferably, the polypeptide is Apo2 ligand or an antibody, including an antibody fragment.

BRIEF DESCRIPTION OF THE DRAWINGS

FIGS. 1A–1E show the complete nucleotide and encoded amino acid sequences (SEQ ID NOS:1 and 2, respectively) of the expression cassette for preparation of pY0317, a production plasmid for anti-VEGF Fab. Residues in bold denote the CDR residues from the original murine A.4.6.1 antibody. Residues in italics and underlined denote murine framework residues that were required for antigen binding.

FIGS. 2A and 2B show a plasmid diagram for pY0317 (FIG. 2A) as well as plasmid construction of pY0317tet20 (FIGS. 2A and 2B).

FIG. 4 shows the nucleotide sequence of human Apo-2 ligand cDNA (SEQ ID NO:3) and its derived amino acid sequence (SEQ ID NO:4). The "N" at nucleotide position 447 (in SEQ ID NO:3) is used to indicate the nucleotide base may be a "T" or "G".

FIG. 10 depicts the humanized anti-CD18 kappa LC sequence (SEQ ID NO:5) with calculated pI values of postulated LC degradation products. The highlighted cleavages with slashes were confirmed by mass spectrometry. See Table 3 below.

DETAILED DESCRIPTION OF THE PREFERRED EMBODIMENTS

Definitions

Figure 2A:
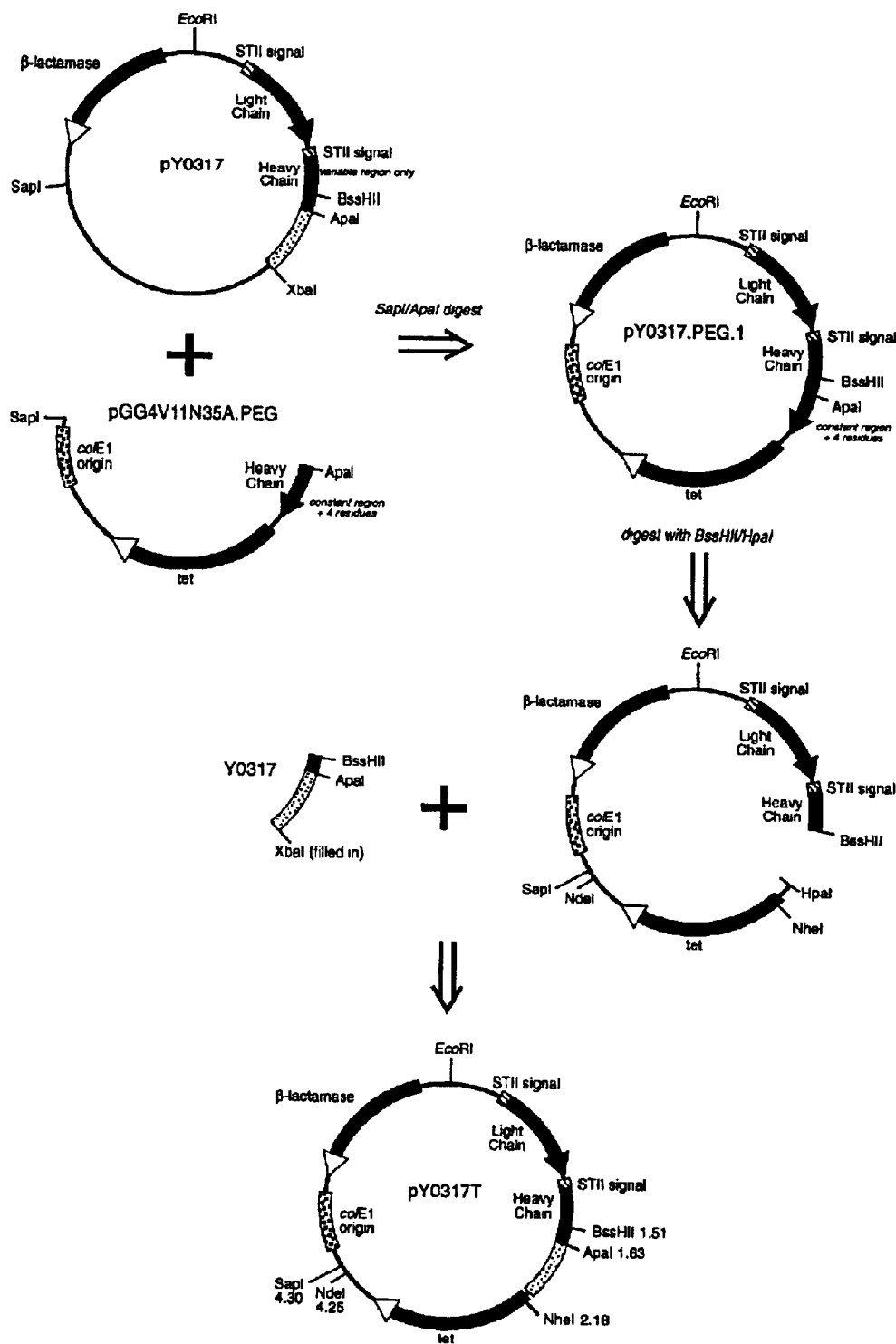

As used herein, "polypeptide" refers generally to peptides and proteins having more than about ten amino acids. "Heterologous" polypeptides are those polypeptides foreign to the host cell being utilized, such as a human protein produced by *E. coli*. While the polypeptide may be prokaryotic or eukaryotic, preferably it is eukaryotic, more preferably mammalian.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; l-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or 6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; Apo2 ligand; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred polypeptides of interest include polypeptides such as HSA, BSA, anti-IgE, anti-CD20, anti-IgG, t-PA, gp120, anti-CD11a, anti-CD18, 2C4, anti-VEGF, VEGF, TGF-beta, activin, inhibin, anti-HER-2, DNase, IGF-I, IGF-II, brain IGF-I, growth hormone, relaxin chains, growth hormone releasing factor, insulin chains or proinsulin, NGF, NT-3, BDNF, Apo2 ligand, and urokinase. Particularly preferred mammalian polypeptides are antibodies, which include full-length antibodies, antibody fragments, and Apo2 ligand. More preferably, these antibodies are human or humanized antibodies. These include, e.g., anti-IgE, anti-IgG, anti-Her-2, anti-CD11a, anti-CD18, anti-CD20, and anti-VEGF, 2C4, BSA, or HSA. Still more preferably, the antibody is an anti-CD18, anti-VEGF, anti-tissue factor, 2C4, anti-Her-2, anti-CD20, anti-CD40, or anti-CD11a antibody. Antibody fragments encompassed within the definition of polypeptide include, for example, a Fab, Fab', Fab'2, or Fab'2-leucine zipper (LZ), and most preferably are anti-CD18 Fab'2-LZ, anti-tissue factor Fab'2 LZ-6× his, anti-VEGF Fab, anti-CD8 his-tagged Fab'2 LZ, and anti-CD18 lys-tagged Fab'2LZ.

As used herein, the descriptor "proteolytically sensitive" for polypeptides refers to polypeptides that are prone to be cleaved, susceptible to cleavage, or cleaved by one or more E. coli proteases, either in the native state or during secretion.

"High-cell-density" fermentation or culturing refers to a process in which typically first some nutrients are added in batches to allow cell growth and take advantage of the relation between $O_2$ consumption and glucose consumption to use dissolved oxygen, which is easy to measure, to control glucose addition. To reach higher cell densities, ammonia may be added continuously, and additional minor nutrients (for example, P, K, S, and Mg) may be added at certain stages of the fermentation to support cell growth, as detailed further in the Examples below.

A "mutant spr gene, the product of which gene suppresses growth phenotypes exhibited by strains harboring prc mutants," refers to an E. coli prc suppressor (spr) (encoding Prc51") with the sequence reported by Hara et al., 1996, supra. Le. MVKSQPILRYILRGIPAIAVAVLLSACSANN TAKNMHPETRAVGSETSSLQASQDEFEN-LVRNVDVICSRIMDQYADWKGVRYRLGGSTKKG IDCSGFVQRTFREOFGLEL-PRSTYEQQEMGKSVSRSNLRTGDLVL-FRAGSTGRHYGIYTGNN QFVHASTSSGVIISSM-NEPYWKKRYNEARRVLSRS (SEQ ID NO:11), wherein the signal sequence is from amino acids 1–26 and the mature protein begins at position 27, so as to have the sequence CSANNTAKNMHPETRAVGSETSSLQASQ-DEFENLVRNVDVKSRIMDQYADWKGV RYRLGGST-KKGIDCSGFVQRTFREQFGLEL-PRSTYEQQEMGKSVSRSNLRTGDLVLFRAG STGRHVGIYIGNNQFVHASTSSGVI-ISSMNEPYWKKRYNEARRVLSRS (SEQ ID NO:12), or one that is mutated, provided that the gene product functions as a suppressor of growth phenotypes of strains with prc mutants. Preferably, the mutation consists of one point mutation. Most preferred is the point mutation W148R in which a TGG codon is changed to CGG, which results in a change of tryptophan to arginine at amino acid 148 of the mature protein SEQ ID NO:12.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Koehler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624–628 (1991) and Marks et al., J. Mol. Biol., 222: 581–597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81: 6851–6855 (1984)). Chimeric antibodies of interest herein include "primatized" antibodies comprising variable-domain antigen-binding sequences derived from a non-human primate (e.g. Old World Monkey, Ape etc) and human constant-region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one that comprises an antigen-binding variable region as well as a light-chain constant domain (CL) and heavy-chain constant domains, $C_H1$, $C_H2$ and $C_H3$. The constant domains may be native-sequence constant domains (e.g. human native-sequence constant domains) or an amino acid sequence variant thereof. Preferably, the intact antibody has one or more effector functions.

Antibody "effector functions" refer to those biological activities attributable to the Fc region (a native-sequence Fc region or Fc region with amino acid sequence variation) of an antibody. Examples of antibody effector functions include C1q binding, complement dependent cytotoxicity, Fc receptor binding, antibody-dependent cell-mediated cytotoxicity (ADCC), phagocytosis, down-regulation of cell-surface receptors (e.g. B cell receptor; BCR), etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcRI only, whereas monocytes express FcRI, FcRII and FcRIII. FcR expression on hematopoietic cells is summarized in Table 3 on page 464 of Ravetch and Kinet, Annu. Rev. Inimunol., 2: 457–492 (1991). To assess ADOC activity of a molecule of interest, an in vitro ADOC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADOC activity of the molecule of interest may be assessed in vivo, e.g., in an animal model such as that disclosed in Clynes et al. Proc. Natl. Acad. Sci. USA. 95: 652–656 (1998).

"Human effector cells" are leukocytes that express one or more FcRs and perform effector functions. Preferably, the cells express at least FcRIII and perform ADCC effector function. Examples of human leukocytes that mediate ADCC include peripheral blood mononuclear cells (PBMC), natural killer (NK) cells, monocytes, cytotoxic T cells, and neutrophils, with PBMCs and NK cells being preferred. The effector cells may be isolated from a native source thereof, e.g. from blood or PBMCs as described herein.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light-chain and the heavy-chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cellular cytotoxicity (ADCC).

The term "hypervariable region" when used herein refers to the amino acid residues of an antibody that are responsible for antigen binding. The hypervariable region generally comprises amino acid residues from a "complementarity-determining region" or "CDR" (e.g. residues 24–34 (L1), 50–56 (L2) and 89–97 (L3) in the light-chain variable domain and 31–35 (H1), 50–65 (H2) and 95–102 (H3) in the heavy-chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g. residues 26–32 (L1), 50–52 (L2) and 91–96 (L3) in the light-chain variable domain and 26–32 (H1), 53–55 (H2) and 96–101 (H3) in the heavy-chain variable domain; Chothia and Lesk, J. Mol. Biol., 196: 901–917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the $V_H$–$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy-chain CHI domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies from any vertebrate species can be assigned to one of two clearly distinct types, called kappa (η) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv, see Plückthun in *The Pharmacology of Monoclonal Antibodies,* vol. 113, Rosenburg and Moore eds. (Springer-Verlag, New York, 1994), pp. 269–315. Anti-ErbB2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90: 6444–6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody), such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature,* 321: 522–525 (1986); Riechmann et al., *Nature,* 332: 323–329 (1988); and Presta, *Curr. Op. Struct. Biol.,* 2: 593–596 (1992).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells, since at least one component of the antibody's natural environment will not be present. Ordinarily, however, isolated antibody will be prepared by at least one purification step.

The expression "control sequences" refers to DNA sequences necessary for the expression of an operably linked coding sequence in a particular host organism. The control sequences that are suitable for prokaryotes include a promoter, optionally an operator sequence, and a ribosome binding site.

Nucleic acid is "operably linked" when it is placed into a functional relationship with another nucleic acid sequence. For example, DNA for a presequence or secretory leader is operably linked to DNA for a polypeptide if it is expressed as a pre-protein that participates in the secretion of the polypeptide; a promoter is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. Linking is accomplished by ligation at convenient restriction sites. If such sites do not exist, the synthetic oligonucleotide adaptors or linkers may be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Modes for Carrying Out the Invention

The present invention provides *E. coli* strains deficient in chromosomal degP and prc encoding protease DegP and Prc, respectively, and harboring a mutant spr gene, the product of which gene suppresses growth phenotypes exhibited by strains harboring prc mutants. The strain is optionally further deficient in chromosomal ptr3 encoding Protease III and/or in chromosomal ompT encoding protease OmpT.

In another embodiment, the strain comprises nucleic acid encoding a polypeptide heterologous to the strain. The strain is preferably transformed with the nucleic acid, which is preferably DNA (cDNA or genomic DNA), as by use of a recombinant expression vector.

In a further aspect, the invention provides a method for producing such heterologous polypeptide. In this method the above *E. coli* strain, which also comprises nucleic acid encoding the polypeptide, is cultured such that the nucleic acid is expressed. Then the polypeptide is recovered from the strain. The recovery may be from the periplasm or culture medium of the strain. Preferably, the culturing takes place in a fermentor, and more preferably under conditions of high cell-density fermentation.

Culturing parameters are used and polypeptide production is conducted in a conventional manner, such as those procedures described below.

A. Selection of Nucleic Acid and Modifications Thereof

The nucleic acid encoding the polypeptide of interest is suitably RNA, cDNA, or genomic DNA from any source, provided it encodes the polypeptide(s) of interest. Methods are well known for selecting the appropriate nucleic acid for expression of heterologous polypeptides (including variants thereof) in *E. coli*.

If monoclonal antibodies are being produced, DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed into the bacterial host cells herein to obtain the synthesis of monoclonal antibodies in the recombinant host cells. Review articles on recombinant expression in bacteria of DNA encoding the antibody include Skerra et al., *Curr. Opinion in Immunol.*, 5: 256–262 (1993) and Plückthun, *Immunol. Revs.*, 130: 151–188 (1992).

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321: 522–525 (1986); Riechmann et al., *Nature*, 332: 323–327 (1988); Verhoeyen et al., *Science*, 239: 1534–1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151: 2296 (1993); Chothia et al., *J. Mol. Biol.*, 196: 901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89: 4285 (1992); Presta et al., *J. Immunol.*, 151: 2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody or affinity-matured antibody are contemplated. For example, the humanized antibody or affinity-matured antibody may be an antibody fragment, such as a Fab, that is optionally conjugated with one or more targeting agent(s) in order to generate an immunoconjugate. Alternatively, the humanized antibody or affinity-matured antibody may be an intact antibody, such as an intact IgG1 antibody.

Fab'-SH fragments can be directly recovered from *E. coli* and chemically coupled to form $F(ab')_2$ fragments (Carter et al., *Bio/Technology*, 10: 163–167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single-chain Fv fragment (scFv) (WO 93/16185; U.S. Pat. Nos. 5,571,894 and 5,587,458). The antibody fragment may also be a "linear antibody", e.g., as described in U.S. Pat. No. 5,641,870. Such linear antibody fragments may be monospecific or bispecific.

Bispecific antibodies are antibodies that have binding specificities for at least two different epitopes. Exemplary bispecific antibodies may bind to two different epitopes of the protein. Bispecific antibodies can be prepared as full-length antibodies or antibody fragments (e.g., $F(ab')_2$ bispecific antibodies).

According to a different approach, antibody variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable bacterial host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies: see, for example, Suresh et a!., Methods in Enzymology, 121: 210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360. WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab'-SH fragments can be directly recovered from E. coli and chemically coupled to form bispecific antibodies (Shalaby et al, J. Exp. Med., 175: 217–225 (1992)).

Various techniques for making and isolating bispecific antibody fragments directly from recombinant cell culture have also been described. For example, bispecific antibodies have been produced using leucine zippers (Kostelny et al.,J. Immunol., 148: 1547–1553 (1992)). The leucine zipper peptides from the Fos and Jun proteins are linked to the Fab' portions of two different antibodies by gene fusion. The antibody homodimers are reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90: 6444–6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported (Gruber et al., J. Immunol., 152: 5368 (1994)).

Antibodies with more than two valencies are contemplated. For example, trispecific antibodies can be prepared (Tutt et al., J. Immunol., 147: 60 (1991)).

Nucleic acid molecules encoding polypeptide variants are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, or cassette mutagenesis of an earlier prepared variant or a non-variant version of the polypeptide.

It may be desirable to modify the antibody of the invention with respect to effector function, e.g., so as to enhance Fc receptor binding. This may be achieved by introducing one or more amino acid substitutions into an Fc region of the antibody. Alternatively or additionally, cysteine residue(s) may be introduced in the Fc region, thereby allowing interchain disulfide bond formation in this region.

To increase the serum half life of the antibody, one may incorporate a salvage receptor binding epitope into the antibody (especially an antibody fragment) as described in U.S. Pat. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Other modifications of the antibody are contemplated herein. For example, the antibody may be linked to one of a variety of nonproteinaceous polymers, e g., polyethylene glycol, polypropylene glycol, polyoxyalkylenes, or copolymers of polyethylene glycol and polypropylene glycol.

B. Insertion of Nucleic Acid Into a Replicable Vector

The heterologous nucleic acid (e.g., cDNA or genomic DNA) is suitably inserted into a replicable vector for expression in the bacterium under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with E. coli hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene, 2: 95 (1977)). pBR322 contains genes for ampicillin and tetracycline resistance and thus provides easy means for identifying transformed cells. The pBR322 plasmid, or other bacterial plasmid or phage, also generally contains, or is modified to contain, promoters that can be used by the E. coli host for expression of the selectable marker genes.

(i) Signal Sequence Component

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell.

For prokaryotic host cells that do not recognize and process the native or a eukaryotic polypeptide signal sequence, the signal sequence is substituted by a prokaryotic signal sequence selected, for example, from the group consisting of the alkaline phosphatase, penicillinase, lpp, or heat-stable enterotoxin II leaders.

(ii) Origin of Replication Component

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria such as E. coli.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for Bacilli.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., J. Molec. Anul. Genet. 1: 327 (1982)), mycophenolic acid (Mulligan et al., Science, 209: 1422 (1980)) or hygromycin (Sugden et a!., Mol. Cell. Biol., 5: 410–413 (1985)). The three examples given above employ bacterial genes under eukaryotic control to convey resistance to the appropriate drug G418 or neomycin (geneticin), xgpt (mycophenolic acid), or hygromycin, respectively.

(iv) Promoter Component

The expression vector for producing the polypeptide of interest contains a suitable promoter that is recognized by the host organism and is operably linked to the nucleic acid encoding the polypeptide of interest. Promoters suitable for use with prokaryotic hosts include the beta-lactamase and lactose promoter systems (Chang et al., Nature, 275: 615 (1978); Goeddel et al., Nature, 281: 544 (1979)), the arabinose promoter system (Guzman et al., J. Bacteriol., 174: 7716–7728 (1992)), alkaline phosphatase, a tryptophan (trp) promoter system (Goeddel, Nucleic Acids Res., 8: 4057 (1980) and EP 36,776) and hybrid promoters such as the tac promoter (deBoer et al., Proc. Natl. Acad. Sci. USA, 80: 21–25 (1983)). However, other known bacterial promoters are suitable. Their nucleotide sequences have been published, thereby enabling a skilled worker operably to ligate them to DNA encoding the polypeptide of interest (Siebenlist et al., Cell, 20: 269 (1980)) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

(v) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform E. coli K12 strain 294 ($ATCC_{31,446}$) or other strains, and successful transformants are selected by ampicillin or tetracycline resistance where appropriate. Plasmids from the transformants are prepared, analyzed by restriction endonuclease digestion, and/or sequenced by the method of Sanger et al., Proc. Natl. Acad. Sci. USA, 74: 5463–5467 (1977) or Messing et al, Nucleic Acids Res., 9:309 (1981), or by the method of Maxam et al., Methods in Enzymology, 65:499 (1980).

C. Selection and Transformation of Host Cells

E. coli hosts suitable as parental hosts for expression plasmids herein include E. coli W3110 ($ATCC_{27,325}$), E. coli 294 ($ATCC_{31,446}$), E. coli B, and E. coli X1776 ($ATCC_{31,537}$). These examples are illustrative rather than limiting. Mutant cells of any of the above-mentioned strains may also be employed as the starting hosts that are then further mutated to contain at least the minimum genotype required herein. E. coli strain W3110 is a preferred parental host because it is a common host strain for recombinant DNA product fermentations. Examples of starting E. coli hosts to be used as parent hosts, along with their genotypes, are included in the table below:

| Strain | Genotype |
| --- | --- |
| W3110 | K-12 F"lambda"IN(rrnD-rrnE)1 |
| 1A2 | W3110 ΔfhuA |
| 9E4 | W3110 ΔfhuA ptr3 |
| 27A7 | W3110 ΔfhuA ptr3 phoAΔE15 Δ(argF-lac)169 |
| 27C6 | W3110 ΔfhuA ptr3 phoAΔE15 Δ(argF-lac)169 ΔompT |
| 27C7 | W3110 ΔfhuA ptr3 phoAΔE15 Δ(argF-lac)169 ΔompT degP41 (ΔpstI-kan$^R$) |
| 33D3 | W3110 ΔfhuA ptr3 lacIq lacL8 ΔompT degP41 (ΔpstI-kan$^R$) |

-continued

| Strain | Genotype |
|---|---|
| 36F8 | W3110 ΔfhuA phoAΔE15 Δ(argF-lac)169 ptr3 degP41 (ΔpstI-kan$^R$) ilvG2096$^R$ |
| 43D3 | W3110 ΔfhuA ptr3 phoAΔE15 Δ(argF-lac)169 ΔompT degP41 (ΔPstI-kan$^R$) ilvG2096$^R$ |
| 43E7 | W3110 ΔfhuA Δ(argF-lac)169 ΔompT ptr3 phoAΔE15 degP41 (ΔpstI-kan$^S$) ilvG2096$^R$ |
| 44D6 | W3110 ΔfhuA ptr3 Δ(argF-lac)169 degP41 (ΔpstI- kan$^S$) ΔompT ilvG2096$^R$ |
| 45F8 | W3110 ΔfhuA ptr3 Δ(argF-lac)169 degP41 (ΔpstI- kan$^S$) ΔompT phoS* (T10Y) ilvG2096$^R$ |
| 45F9 | W3110 ΔfhuA ptr3 Δ(argF-lac)169 degP41 (ΔpstI- kan$^S$) ΔompT ilvG2096$^R$ phoS* (T10Y) Δcyo::kan$^R$ |

Also suitable are the intermediates in making strain 36F8, i.e., 27B4 (U.S. Pat. No. 5,304,472) and 35E7 (a spontaneous temperature-resistant colony isolate growing better than 27B4). An additional suitable strain is the *E. coli* strain having the mutant periplasmic protease(s) disclosed in U.S. Pat. No. 4,946,783 issued Aug. 7, 1990.

The strains of this invention may be produced by chromosomal integration of the parental strain or other techniques, including those set forth in the Examples below.

The nucleic acid encoding the polypeptide is inserted into the host cells. Preferably, this is accomplished by transforming the host cells with the above-described expression vectors and culturing in conventional nutrient media modified as appropriate for inducing the various promoters.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for prokaryotic cells or other cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation.

D. Culturing the Host Cells

Prokaryotic cells used to produce the polypeptide of interest are cultured in suitable media as described generally in Sambrook et al., supra. The culture conditions, such as temperature, pH, and the like, are those previously used with the host cell selected for expression, and will be apparent to the ordinarily skilled artisan.

Where the alkaline phosphatase promoter is employed, *E. coli* cells used to produce the polypeptide of interest of this invention are cultured in suitable media in which the alkaline phosphatase promoter can be partially or completely induced as described generally, e.g., in Sambrook et al, supra. The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

Any other necessary media ingredients besides carbon, nitrogen, and inorganic phosphate sources may also be included at appropriate concentrations introduced alone or as a mixture with another ingredient or medium such as a complex nitrogen source. The pH of the medium may be any pH from about 5–9, depending mainly on the host organism.

If the promoter is an inducible promoter, for induction to occur, typically the cells are cultured until a certain optical density is achieved, e.g., a $A_{550}$ of about 200 using a high-cell-density process, at which point induction is initiated (e.g., by addition of an inducer, by depletion of a medium component, etc.), to induce expression of the gene encoding the polypeptide of interest.

E. Detecting Expression

Gene expression may be measured in a sample directly, for example, by conventional Southern blotting, northern blotting to quantitate the transcription of mRNA (Thomas, *Proc. Natl. Acad. Sci. USA*, 77: 5201–5205 (1980)), dot blotting (DNA analysis), or in situ hybridization, using an appropriately labeled probe, based on the sequences of the polypeptide. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, assays or gels may be employed for detection of protein.

For secretion of an expressed gene product, the host cell is cultured under conditions sufficient for secretion of the gene product. Such conditions include, e.g. temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

F. Purification of Polypeptides

The following procedures, individually or in combination, are exemplary of suitable purification procedures, with the specific method(s) used being dependent on the type of polypeptide: fractionation on immunoaffinity or ion-exchange columns; ethanol precipitation; reversed-phase HPLC; hydrophobic-interaction chromatography; chromatography on silica; chromatography on an ion-exchange resin such as S-SEPHAROSE™ and DEAE; chromatofocusing; SDS-PAGE; ammonium-sulfate precipitation; and gel filtration using, for example, SEPHADEX™ G-75.

The monoclonal antibodies may be suitably separated from the culture medium by conventional antibody purification procedures such as, for example, protein A-Sepharose, hydroxylapatite chromatography, gel electrophoresis, dialysis, or affinity chromatography.

The invention will be more fully understood by reference to the following examples. They should not, however, be construed as limiting the scope of the invention. All literature and patent citations herein are incorporated by reference.

EXAMPLE 1

Material and Methods

A. Expression Plasmids

1. Plasmids for Expressing rhuFab'2 LZ (xCD18) and Tagged Derivatives pS1130

Plasmid pS1130 is a pBR322-based plasmid described in U.S. Pat. Nos. 6,180,367 and 6,258,560. The rhuFab'2 LZ (xCD18) synthesis is regulated by the *E. coli* alkaline phosphatase (AP) promoter. When the AP promoter is induced by phosphate depletion, it forms a di-cistronic messenger RNA in the order of STII signal-kappa light-chain coding sequence; STII signal-heavy-chain coding sequence, followed by a leucine zipper sequence. A lambda transcription terminator was placed near the translation termination codon.

pcyc34

Plasmid pcyc34 is a tacII promoter counterpart of pS1130.

pxCD18-7T3

The dual-promoter plasmid containing two separate translational units, pxCD18-7T3, allows for the temporal separation of transcription of light chain from the transcription of heavy chain. As in pSI 130, the light chain remains under the control of the phoA promoter. However, in pxCD 18-7T3, a $\lambda t_0$ transcriptional terminator follows the light-chain coding sequence. Downstream of this terminator, the tacII promoter was added to control the transcription of the heavy-chain fragment/C-terminal leucine zipper (DeBoer et al., *Proc. Natl. Acad. Sci. USA*. 80: 21–25 (1983)). A second $\lambda t_0$ transcriptional terminator follows this coding sequence. Silent codon variants of the STII signal sequence were used to direct the secretion of both chains (Simmons and Yansura, *Nature Biotechnoloav*, 14: 629–634 (1996)). Specifically, the nucleotides in the STII signal sequence were modified such that the light chain had a TIR relative strength of 7 and the heavy chain had a TIR relative strength of 3, and the last three nucleotides of the signal sequence preceding both the light and heavy chains were GCT. In this two-promoter system the phoA promoter sequence and the DNA for the light and heavy antibody chains are the same as in pS1130.

pAB3

Plasmid pAB3 is designed to express an anti-CD18 F(ab')2 in the *E. coli* periplasm under the control of the alkaline phosphatase promoter (Kikuchi et al., *Nucleic Acids Res.*, 9 (21): 5671–5678 (1981)) and has a leucine zipper and is His-tagged. The heat-stable enterotoxin II signal sequence (Picken et al., *Infect. Immun.*, 42: 269–275 (1983)) precedes the light and heavy chains, and onto the C-terminal end of the heavy chain is fused the yeast GCN4 leucine zipper followed by six histidine residues. The light- and heavy-chain coding sequences are in a polycistronic configuration with the $\lambda_o$ transcriptional terminator (Scholtissek and Grosse, *Nucleic Acids Res.*, 15: 3185 (1987)) following the heavy-chain gene.

The plasmid pAB3 was constructed by ligating together three DNA fragments, the first of which was the vector pS1130 in which the small KpnI-SphI fragment had been removed. The second part in the ligation was an approximately 645 base-pair KpnI-HindIII fragment from pS1130. The final part in the ligation was a synthetic DNA duplex with the following sequence:

(SEQ ID NO:6)
5'-AGCTTGTCGGGGAGCGCCATCACCATCACCATCACTAAGCATG (SEQ ID NO:7)
ACAGCCCCTCGCGGTAGTGGTAGTGGTAGTGATTC-5' pAB21

Plasmid pAB21 is a derivative of pAB3 in which the six histidine residues on the C-terminal end of the heavy chain have been replaced with six lysine residues. This plasmid was constructed in an identical manner as pAB3 except that the synthetic DNA used in the ligation was the following:

(SEQ ID NO:8)
5'-AGCTTGTCGGGGAGCGCAAAAAGAAAAAGAAAAAGTAAGCATG (SEQ ID NO:9)
ACAGCCCCTCGCGTTTTTCTTTTTCTTTTTCATTC-5'

Plasmid for expressing anti-TF Fab'2 LZ-6xhis

Plasmid D3H44-F(ab')2 (also known as pD3h44f2), constructed to direct production of anti-tissue factor Fab'2 leucine zipper—6xhis, has exactly the same backbone DNA sequence as pAB3 except that the variable regions for HC and LC were changed from xCD18 VL/VH to xTF VL/VH. The construction of this plasmid is described in WO 01/70984 published Sep. 27, 2001.

Specifically, first, the plasmid for expressing anti-TF Fab (D31H44-F(ab)) was prepared as follows: The plasmid pEMXI used for mutagenesis and expression of F(ab)s in *E. coli* has been described in Werther et al., *J. Immunol.*, 157: 4986–4995 (1996). Briefly, the plasmid contains a DNA fragment encoding a consensus human η subgroup I light chain (VLKI-CL), a consensus human subgroup III heavy chain (VHIII-CH1) and an alkaline phosphatase promoter. The use of the consensus sequences for VL and VH has been described in Carter et al, *Bio/Technology*, 10: 163–167 (1992); Carter et al., *Proc. Natl. Acad. Sci. USA*, 89: 4285–4289 (1992).

Site-directed mutagenesis (Kunkel, *Proc. Natl. Acad. Sci. USA*, 82: 488–492 (1985)) was performed on a deoxyuridine-containing template of pEMX 1. The six CDRs were changed to the murine D3 sequence; the residues included in each CDR were from the sequence-based CDR definitions (Kabat et al., *Sequences of proteins of immunological interest*, Ed. 5, Public Health Service (National Institutes of Health, Bethesda, Md., (1991)), except for CDR-H1, which was defined using a combination of CDR-H1 definitions from Kabat et al, supra, and Chothia et al., *Nature*, 342: 877–833 (1989), i.e., CDR-H1 was defined as extending from residues H26–H35 in the heavy chain. D3H44-F(ab) therefore encoded a F(ab) consisting of a complete human framework (VL_η subgroup I and VH subgroup III) with the six complete murine CDR sequences.

D3H44-F(ab')2 was generated by the addition of the heavy-chain hinge (CPPCPAPELLGG; SEQ ID NO:10) to the C-terminus of the D3H44-F(ab), followed by the GCN4 leucine zipper and a (his)6 tag for purification (see the description for pAB3 above for the leucine zipper and hisx6 tag).

3. Plasmids for Expressing Anti-VEGF Fab pY0317

The affinity-matured anti-VEGF Fab protein Y0317 is described in Chen et al., *J. Mol. Biol.*, 293: 865–881(1999). For constructing a plasmid to produce it, pYO317, briefly, an expression cassette was cloned into the framework of the *E. coli* plasmid pBR322 at the EcoRI site (Sutcliffe, Cold Spring Harbor *Symp. Quant Biol.* 43: 77–90 (1978)). The expression cassette contained at least the following basic components: (1)phoA promoter for the control of transcription; (2) $\lambda t_0$ terminator to end transcription; and (3) the Shine-Dalgarno sequence from the E. coli trp or the heat-stable enterotoxin II (STIT) gene, or a combination of both to facilitate translation. The basic components of bacterial expression cassettes are known in the art and have been described in, for example, Kikuchi et al., *Nucleic Acids Res.*, 9(21): 5671–5678 (1981) (for phoA promoter); Scholtissek and Grosse, *Nucleic Acids Res.*, 15: 3185 (1987) (for $\lambda t_0$ terminator); Yanofsky et al., *Nucleic Acids Res.*, 2:6647–6668(1981) (for trp); Picken et al., *Infect. Immun.*, 42: 269–275 (1983) (for STII); and Chang et al., *Gene,* 55: 189–196 (1987) (for combination use of trp and STII Shine-Dalgarno sequence). Additionally, the STII signal sequence or silent codon variants thereof preceded the coding sequence for both light and heavy chains in pY0317 for producing anti-VEGF Fab and directed the secretion of the protein into the periplasm. Picken et al., *Infect. Immun.,* 42: 269–275 (1983); Simmons and Yansura, *Nature Biotechnology,* 14: 629–634 (1996). The nucleotide and amino acid sequences for the 1952-base-pair expression cassette inserted into the EcoRI site for recombinant protein production are shown in FIG. 1 (SEQ ID NOS: 1 and 2, respectively).

RhuFab V2 Y0317 was created by humanization of the murine A.4.6.1 (Presta et al., *Cancer Res.,* 57: 4593–4599 (1997) monoclonal antibody using a process previously described for other antibodies (Carter et al., *Proc. Natl. Acad. Sci. USA.* 89: 4285–4289 (1992); Presta et al., *J. Immunol.,* 151: 2623–2632 (1993); Werther et al., *J. Immunol.* 157: 4986–4995 (1996)). Briefly, cDNAs encoding the muMAb A.4.6.1 variable light and variable heavy chains were isolated using RT-PCR from hybridoma cells producing the murine monoclonal antibody. These cDNAs were cloned and fused to human CL and human CH1 domains (Werther et al., *J. Immunol.,* 157: 4986–4995 (1996)), generating a mouse-human chimeric Fab. The six complement-determining regions (CDRs) (denoted in FIG. 1 in bold type) were transplanted into a previously humanized antibody vector encoding a consensus human κ subgroup I light chain and a consensus human subgroup III heavy chain (Carter et al., *Proc. Natl. Acad. Sci. USA,* 89: 4285–4289 (1992)). Transferring just the CDR residues into the human framework caused a 1000-fold reduction in binding to the VEGF antigen. Several framework residues near the CDRs (denoted in FIG. 1 in italicized and underlined type) also were changed to improve binding to the target (Presta et al., *Cancer Res.* 57: 4593–4599 (1997)). In all, seven heavy-chain residues and one light-chain residue were changed outside of the CDRs. The heavy and light chains were then moved into a phage-display vector (Baca et al., *J. Biol. Chem.* 272: 10678–10684 (1997)), replacing the hGH gene of phGHam-g3 (Bass et al., *Proteins,* 8: 309–314 (1990)). Site-directed mutagenesis was used to change VL Met4Leu to preclude methionine oxidation and VH Thr231Leu for ease of cloning to the geneIII fusion. This vector is termed Y0101 and was used as the starting point for optimization of the CDRs in binding to the VEGF antigen (Muller et al., *Structure,* 6: 1153–1167 (1998)). Only mutations in CDRs H1 and H3 were found to improved binding and were incorporated into the final version pY0317. The changes from the pY0101 plasmid to the pY0317 plasmid are: Thr28Asp, Asn31His, His101Tyr, Ser105Thr. All these changes are in the variable heavy-chain region. The pY0317 plasmid is a Fab phage display vector. A plasmid diagram of this plasmid appears in FIG. 2A.

pY0317tet20

Plasmid pY0317tet20 was constructed to direct production of the rhuFab V-2 in *E. coli.* FIGS. 2A and 2B show a flow chart of the plasmid construction, which starts with pY0317. The plasmid pY0317tet20 is a modified version of the well-characterized pBR322 plasmid. The 639-base-pair AvaI-PvuII fragment has been removed from the pBR322 portion of the plasmid. This deletion removes the rop gene, which is involved in copy number control (Cesareni et al., *Proc. Natl. Acad. Sci., USA,* 79: 6313–6317 (1982)). Consequently the plasmid has a slightly elevated copy number compared to pBR322. A 1952-base-pair expression cassette (FIG. 1) has been inserted into the EcoRI site for recombinant protein production. Plasmid pY0317tet20 is resistant to both tetracycline and β-lactam antibiotics. The expression cassette contains a single copy of the light chain and heavy chain linked in tandem. Transcription of each gene into a single dicistronic mRNA is directed by the *E. coli* phoA promoter (Chang et al., *Gene,* 44: 121–125 (1986)). Translation-initiation signals for each chain are provided by *E. coli* STII (heat-stable enterotoxin) Shine-Dalgarno sequences. Translation of each chain begins with a 23-residue STII signal peptide (Picken et al, *Infection and Immunity,* 42: 269–275 (1983)) that directs translocation of the peptides across the cytoplasmic membrane into the periplasmic space. The STII signal peptide is then removed by the *E. coli* leader peptidase. The light and heavy chains fold into their native conformations after secretion into the periplasm and are covalently joined by an intermolecular disulfide bond.

Tetracycline resistance was placed on the final vector through modifications of pY0317 (see FIGS. 2A and 2B). A 3642-base-pair SapI/ApaI fragment of pY0317, which includes the origin of replication of pBR322, the β-lactamase gene, the phoA promoter, the entire light chain, and the amino-terminal half of the heavy chain (VH), was ligated to a 2738-base-pair SapI/ApaI fragment of p6G4V11N35A.PEG. This second fragment contains the CH1 region of the heavy chain and the tetracycline-resistance gene from pBR322. This fragment also contains four extra amino acids at the carboxyl terminus of the heavy chain for site-specific modification of the protein. The region containing the four extra residues and the CH1 region were removed with a BssHII/HpaI digest and replaced with the BssHII/XbaI fragment of pY0317, restoring the original heavy-chain sequence and deleting the site-specific modification region. The XbaI digest was performed first and the overhang filled in with Klenow and deoxynucleotides. This was followed by the BssHII digest gel purification of the 433-base-pair fragment. A final manipulation of the plasmid was performed replacing the NheI-to-NdeI fragment of pBR322 with a NheI/NdeI fragment of pBR322 containing a 639-base-pair AvaI-PvuII deletion. The final plasmid, pY0317tet20, is resistant to tetracycline and β-lactam antibiotics, and contains the phoA promoter and the genes encoding the light and heavy chains of anti-VEGF.

Figure 3:
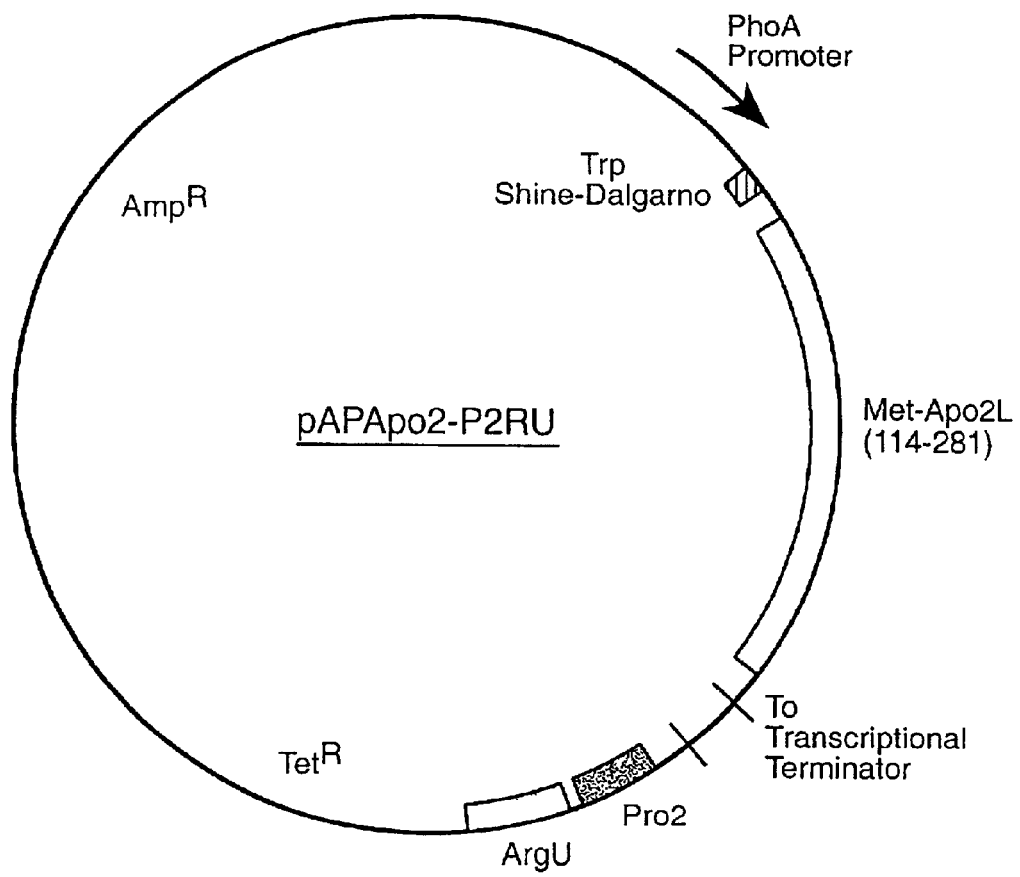
FIG. 3 shows the plasmid diagram for pAPApo2-P2RU.

4. Plasmid for Expressing Apo2L pAPApo2-P2RU is described in WO 01/00832 published Jan. 4, 2001. Briefly, this plasmid, the construct of which is shown in FIG. 3, encodes the co-expression of Apo-2L (amino acid residues 114–281) and the tRNA's encoded bypro2 and argU., which co-expression is regulated by the alkaline phosphatase promoter. The pBR322-based plasmid (Sutcliffe, *Cold Spring Harbor Symp. Quant. Biol.,* 43: 77–90 (1978)) pAPApo2-P2RU was used to produce the Apo-2L in *E. coli.* The transcriptional and translational sequences required for the expression of Apo-2L are provided by the alkaline phosphatase promoter and the trp Shine-Dalgarno, as described for the plasmid phGH1 (Chang et al., *Gene,* 55: 189–196 (1987)). The coding sequence for Apo-2L (from 114–281) is located downstream of the promoter and Shine-Dalgarno sequences and is preceded by an initiation methionine. The coding sequence includes nucleotides (shown in FIG. 4) encoding residues 114–281 of Apo-2L (FIG. 4 (SEQ ID NOS:3 and 4, respectively, for nucleotide and amino acid sequences)) except that the codon encoding residue Pro119 is changed to "CCG" instead of "CCT" in order to eliminate potential secondary structure. The sequence encoding the lambda to transcriptional terminator (Scholtissek et al., *Nucleic Acids Res.*, 15: 3185 (1987)) follows the Apo-2L coding sequence.

Additionally, this plasmid also includes sequences for the expression of the tRNA's pro2 (Komine et al., *J. Mol. Biol.*, 212: 579–598 (1990)) and argU/dnaY(Garcia et al., *Cell*, 45: 453–459 (1986)). These genes were cloned by PCR from *E. coli* W3110 and placed downstream of the lambda $t_o$ transcriptional-terminator sequence. This plasmid confers both tetracycline and ampicillin resistance upon the production host.

B. Cell Transformations

Competent cells of the relevant strain were prepared and transformed with the appropriate plasmid using standard procedures, and successful transformants were selected and grown in culture. For plasmids that were resistant to tetracycline, the transformants were picked from LB plates containing 20 µg/mL tetracycline (LB+Tet20), streak-purified, and grown in LB broth with 20 µg/mL tetracycline in a 30° C. shaker/incubator before being stored in DMSO at −80° C.

In the case of the plasmids pxCD18-7T3 and pcyc34, an additional plasmid, pMS421, was co-transformed along with pxCD18-7T3 or pcyc34. pMS421 is a pSC101-based plasmid that overexpresses lacIq suppressor, which suppresses the induction of the tacII promoter until IPTG was added to de-suppress it, and which also confers spectinomycin and streptomycin resistance. This plasmid provides additional copies of the lacIq chromosomal gene under the control of its own promoter from a lacIq strain, which gene is put into the compatible plasmid $pSC_{101}$.

C. Antibody Extraction

The soluble fraction of *E. coli* cells was prepared by suspending a 20 OD-mL pellet in 500 µL of 200 mM TRIS-HCl (pH 8.0) with 20 µL of 0.1 M EDTA (pH 8.0) and 10 µL of lysozyme (6 mg/mL). This mixture was vortexed, sonicated for 7–10 pulses, then centrifuged at 15,000 rpm for 15 minutes at 4° C. The supernatant fraction after centrifugation is called the high-salt extract (HSE). The remaining pellet was used for insoluble fraction analysis.

D. Protein Identification

The one-dimensional SDS-PAGE gel electrophoresis was carried out in a 4–12% linear acrylamide gradient from Novex. Specifically, the system used was the NOVEX® NuPage™ System, consisting of NuPAGE Bis-TRIS Pre-Cast Gels (for low- to mid-molecular weight proteins).

The two-dimensional gel electrophoresis was carried out as described by Champion et al., *Electrophoresis*, 20 (4–5): 994–1000 (1999)), with immobilized pH gradients (pH 3–10) in the first dimension and a linear acrylamide gradient (9–18% T) in the second dimension, purchased from Amersham Pharmacia Biotech. Protein identification was determined using a combination of silver/Coomassie staining, $NH_2$-terminal sequencing, and mass spectrometric analysis. For analytical gels, *E. coli* cell lysates (~40 µg protein) were combined with rehydration solution as described by Champion et al, supra. Eighteen-cm pH 3–10 non-linear immobilized pH gradient (IPG) gel strips (Amersham Pharmacia Biotech) were used for isoelectric focusing for a total of 50,000 Vh.

Preparatively loaded gels were blotted to polyvinylidene difluoride (PVDF) membranes (ProBlott; Applied Biosystems) as described by the manufacturer. The $NH_2$-terminal sequencing was done using a 20-min Edman cycle and a multiple sample horizontal flow reactor for the sequence analysis of PVDF-electroblotted proteins (Henzel et al., *Analytical Biochemistry*, 267: 148–160 (1999)). The molecular weight of light-chain-specific spots was estimated from MALDI-TOF mass spectrometry and capillary LC-MS of samples eluted from gels (Champion et al, supra).

E. Measurement of the Target Protein Species

The AME5™—reverse-phase dual-column assay (AME5™/RP dual-column assay) was used for anti-CD18 F(ab')2 LZ titer determination, as described below.

F. AME5™/RP Dual-Column Assay

1. Instrumentation and Equipment

An INTEGRAL™ workstation (from PerSeptive Biosytems) was set up in the dual-column gradient configuration. An affinity column containing an anti-light-chain (kappa) Fab antibody (AME5™) immobilized on controlled-pore glass (CPG) was used to capture the target protein. A reversed-phase column, temperature controlled at 60° C., was used to further resolve the captured antibody species. Activated aldehyde immunoaffinity resin (AL-20), reversed-phase POROS resins (R220), and column-packing devices were obtained from PerSeptive Biosytems, (Cambridge, Mass., USA). CPG Empty PEEK columns, 30×2.1 mm (100 µl), were purchased from Upchurch Scientific (Oak Harbor, Wash., USA). *E. coli* samples were filtered using ACRODISC™ PF syringe 5-micron filters (from Gelman Sciences).

2. Purification of AME5™ Anti-Human Kappa FAb (his-gly)$_4$ his-(lys)

Phosphate-buffered saline, pH 7.2 (PBS) containing 9.4 mM sodium phosphate, 136.9 mM sodium chloride, and 2.7 mM potassium chloride is referred to herein as loading buffer. Monoclonal antibodies were obtained from a murine FAb, AME5™ anti-human kappa FAb (his-gly)$_4$ his-(lys)$_3$, which was purified from *E. coli* paste and is called AME5™ FAb hgk for purposes herein. The *E. coli* paste was obtained from a 10-liter fermentation in 27C7 cells. A microfluidizer was used to homogenize the cells after suspension in 20 mM sodium phosphate, 0.25 M sodium chloride, 10 mM magnesium chloride, and 2 mM imidazole at pH 7.0. The *E. coli* extract was clarified by addition of 0.2% polyethyleneimine (PEI) and centrifugation. The clarified extract was purified using a combination of ion exchange and immobilized metal-ion-chelating (IMAC) chromatography steps. Chelating SEPHAROSE FAST FLOW™ and SP SEPHAROSE FAST FLOW™ resins were from Amersham Pharmacia.

3. Immobilization of AME5™ FAb hgk to Activated Glyceryl-Coated CPG

The purified Fab was immobilized onto periodate-activated glyceryl-coated controlled pore glass (CPG) to make the affinity resin. AME5™ FAb hgk antibody was immobilized onto activated glyceryl-coated CPG using a modification of the method of Roy et al., *J. Chromatography*, 303: 225–228 (1984).

Dry CPG was wetted with purified water, packed into a chromatography column, and activated for 30 minutes by recirculating 1% sodium metaperiodate (Sigma S-1878™) through the column. The activated resin was then washed into 20 mM sodium phosphate, 0.15 M sodium chloride, pH 7.2 (coupling buffer).

AME5™ FAb hgk antibody at a concentration of approximately 5 mg/mL in coupling buffer containing 1 µg/mL of the reducing agent sodium cyanoborohydride (Sigma S8628) was recirculated through the activated resin bed. The coupling of the antibody to the resin was monitored by the decrease in absorption at 280 nm. When there was no further decrease in absorption, any remaining antibody was washed out with coupling buffer and recovered. The coupling density was determined by the difference between the starting amount and the amount recovered after the reaction was completed and is reported in mg FAb per mL of resin.

Any remaining active sites on the resin were then reacted by recirculating 1 M ethanolamine, pH 8.0 (ICN, catalog # 151078) in the presence of 1 μg/mL sodium cyanoborohydride for 2 hours. The resin was then washed into coupling buffer containing 0.01% thimerosal (GDL International) for storage. The resin was precycled three times between equilibration and elution buffers to be used before any protein was applied.

4. Reagents and Assay Method

The solvent reservoirs were: Solvent 1A, affinity loading buffer; Solvent 1B, reversed-phase aqueous buffer and affinity elution buffer, 0.1% TFA in water; Solvent 2A, water. Solvent 2B, reversed-phase organic elution buffer, 0.09% TFA/80% acetonitrile. Fifty μL of E. coli HSEs (diluted 1:2) or the supernatant of the fermentation broth in loading buffer was injected. All forms of anti-CD18 found in fermentation cell extracts were captured by this AME5™ antibody as determined by comparison of 2-D gels of a blank run, a production run, and affinity-captured (AME5™) material from a production run. After non-specific adsorption had been reduced (by washing with PBS), the affinity column was placed in-line with a reversed-phase column and the captured components were transferred by elution with dilute acid. These components were subsequently resolved by eluting the reversed-phase column with a shallow acetonitrile gradient. Detection was performed by measurement of absorbance at 280 nm, and intact antibody was quantified by comparison with peak areas of similarly treated standards.

G. Peak Identification of Chromatogram

This assay resolved anti-CD18 fragments into five antibody-related peaks, which represent the following antibody fragments:

Peak 1: LC-115 (115 amino acids degradation product of kappa light chain)
Peak 2: unassembled free light chain and glutathionated light chain
Peak 3: the light-chain dimer
Peak 4: the Fab-like fragment
Peak 5: the Fab'2-LZ or Fab'2 fragment A purified bulk anti-CD18 F(ab)'2 release material (5 mg/mL) was used as the standard. An E. coli extract derived from a high-cell-density fermentation of 49A5/pS1130 was frozen at −70° C. and used as the positive control. Equal cell mass was loaded for all the samples compared.

H. Total HC/LC POROS™ Reversed-Phase Assay

To assess the total quantity of light-chain and heavy-chain fragments produced in the fermentations, an alternative reversed-phase HPLC assay (RP-HPLC) was used. For total antibody expression 100 μL of whole broth was added with 100 μL of 0.2 M TRIS 8.0. After sonication for 10 pulses, 650 μL of guanidine-HCl/50 mM TRIS, pH 9 and 50 μL of 2M DTT were added and incubated at room temperature for 15 minutes. Before loading to the column, 200 μL of acetonitrile was added and filtered through a size-exclusion spin column (Pharmacia). Five μL of this suspension was analyzed by the POROS™ reversed-phase assay.

For the reversed-phase methodology, a HEWLETT-PACKARD™ 1100HPLC was used with a Perseptive POROS™ R-1 reversed-phase column. Analyses were run with the column heated to 60° C., and UV absorbance at 278 nm was monitored. The column was equilibrated in a 28% acetonitrile solution in water with 0.1% trifluoroacetic acid. Twenty-five μL of sample was next loaded on the column, and elution was performed using a linear gradient from 28% to 38% acetonitrile over 20 minutes, followed by a 17-minute period of regeneration at 95% acetonitrile and re-equilibration at 28% acetonitrile. Peaks for light-chain- and heavy-chain-related species were identified by comparison with standards and analysis using a HEWLETT-PACKARD™ mass selection detector for confirmation. Fermentation samples from a blank run in which the same host was used except with a plasmid not containing the sequences for heavy and light chain, were similarly prepared and analyzed to determine the appropriate baselines for the analyses. Integration of the peak areas was performed using the HEWLETT-PACKARD™ 1100 software, and standards were spiked into blank run samples to generate a calibration curve in order to determine the relative quantity of the various species in the samples.

For the soluble samples lysates were prepared as for the ion-exchange assay. Typically, 100 μL of sample was diluted with 650 μL of 6M guanidine-HCl, 50 mM TRIS-HCl, pH 9. Fifty μL of 2M dithiothreitol (freshly thawed) was then added, followed by 200 μL of acetonitrile, followed by filtration with a 0.2 μm filter prior to loading on the HPLC.

The insoluble lysate samples were also similarly analyzed by resuspending the PBS-washed, insoluble pellets obtained after cell extraction in 100 μL of 0.2 M TRIS 8.0 and mixing well. Then 650 μL of 6M guanidine-HCl 150 mM TRIS-HCl, pH 9, 50 μL of 2M DTT, and 200 μL of acetonitrile were added. The samples were then filtered, and 10 μL of the filtered samples was analyzed using the same method as for the soluble lysate samples.

I. CSX Assay

Digestion of the anti-CD18 Fab'2 LZ was analyzed by HPLC cation-exchange chromatography. Specifically, samples were diluted at least 1:1 and 250 μl were loaded onto a BAKERBONDJ™ carboxy-sulfon (CsX) 50×4.6-mm column (J. T. Baker, Phillipsburg, N.J.) maintained at 55° C. on a Hewlett-Packard 1090HPLC system. Samples were eluted using a gradient of approximately 5 to 50 mM sodium phosphate (pH 7.0) over 14 minutes, and peaks were monitored using UV absorbance at 278 nm. The peak containing anti-CD18 Fab'2-leucine zipper was identified and quantified by comparison with purified standards.

J. Cell Line Constructions

Figure 5:
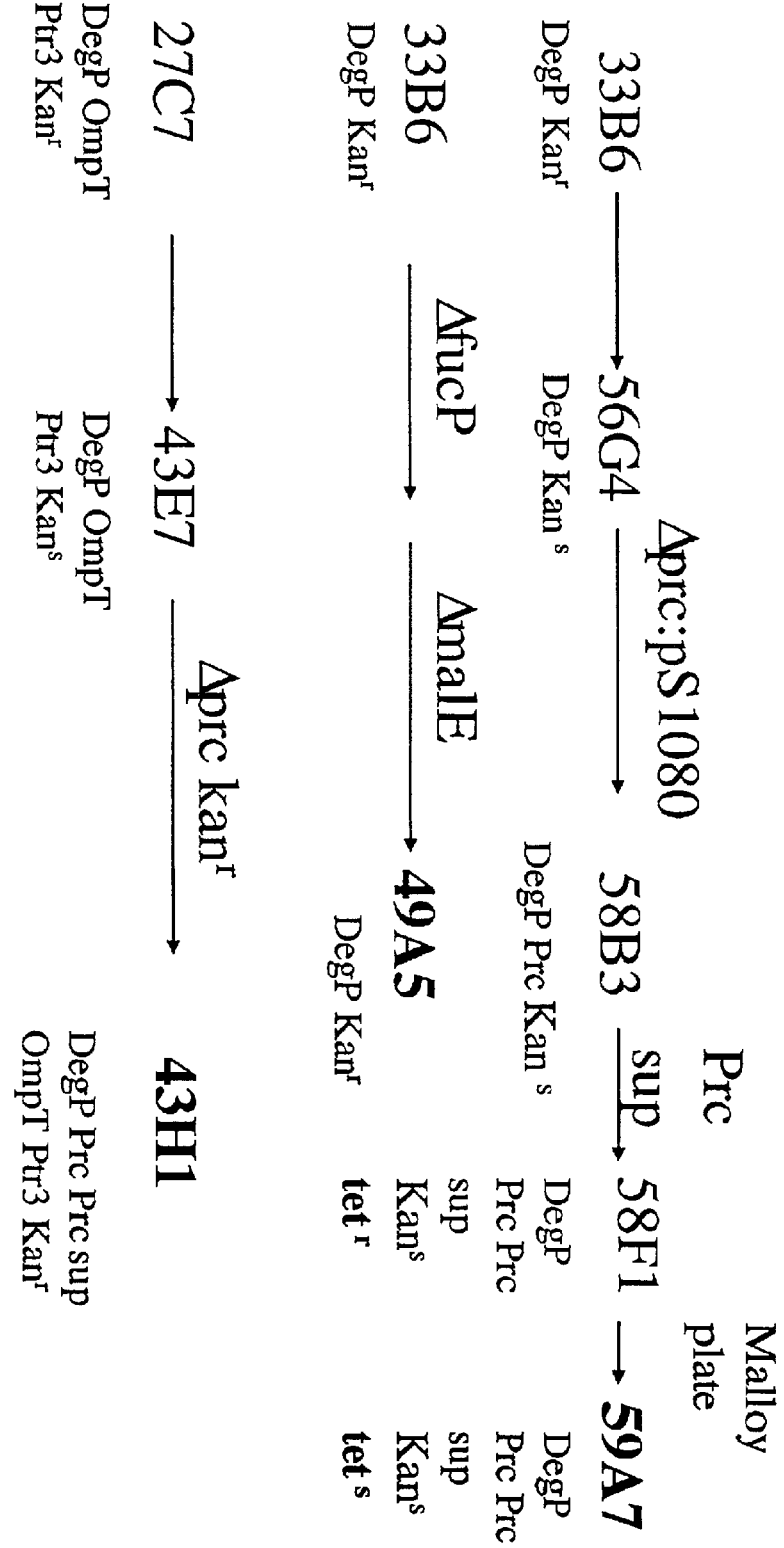
FIG. 5 depicts a diagram of the derivation of *E. coli* strains 59A7, 49A5, and 43H1.

The hosts used in the rhuFab'2 LZ (xCD18) fermentation are derivatives of E. coli W3110 (Bachmann, Cellular and Molecular Biology, vol. 2 (Washington, D.C.: American Society for Microbiology, 1987), pp. 1190–1219), and are designated as follows: 49A5, 58B3, 59A7, 43H1, 58H2, 45F8, 41H1, and 33D3. FIG. 5 depicts a diagram of the derivation of E. coli strains 59A7, 49A5, and 43H1.

1. Strain 49A5

The complete genotype of 49A5 is ΔfhuA phoa ΔE15Δ (argF-lac)169 deoC2 degP41(Δpst1-Kan$^r$) IN(rrD-rrE)1 ilvG2096 (Val$^r$) ΔfucP ΔmalE. The starting strain, E. coli W3110, is a derivative of E. coli K-12 that is F'- and lambda-minus. It has been shown to carry an inversion of the chromosome between rrnD and rrnE (Bachmann., supra; Hill and Hamish, Proc. Natl. Acad. Sci. USA, 78: 7069–7072 (1981)). The fhuA gene (previously designated tonA) was deleted from W3110 by imprecise excision of Tn10 following its insertion into the fhuA gene. The resulting strain, 1A2, is resistant to bacteriophage T1, T5 and ø80.

The two deletion mutations, phoA ΔE15 (Sarthy A. et al., J. Bacteriol., 145: 288–292 (1981)) and Δ(arg-lac)169 (Schweizer et al., Mol. Gen. Genet., 192: 293–294 (1983)), were simultaneously introduced into strain 1A2 by P1 co-transduction with a linked Tn5 insertion in the proC gene. Precise excision of the transposon restored the proC gene. The phoA ΔE15 mutation eliminates alkaline phosphatase expression, and the Δ(argF-lac)169 mutation is responsible for the lac$^-$ phenotype of this strain, which is designated 7C1.

The deoC2 mutation, which eliminated deoxyribose phosphate aldolase expression, was introduced by P1 co-transduction. The deoC locus is genetically linked to the threonine biosynthetic locus. A threonine auxotroph was created by Tn10 insertion and imprecise excision. The threonine auxotroph was then transduced to threonine prototrophy with P1 phage, grown on a deoC2 mutant. The presence of the deoC2 mutation was confirmed by the inability of the resulting strain, 16C9, to grow on 0.2% thymidine as a carbon source.

The degP41(ΔPst1-Kan$_r$) mutation, a mutation in the gene for a periplasmic protease, was introduced by transduction. This mutation was constructed in vitro by replacing a section of the degP gene with a kanamycin-resistance gene (Strauch and Beckwith, *J. Bacteriol.*, 171: 2689–2696 (1989)). This is not a transposon, but allows for selection of the deletion using kanamycin resistance. The resulting strain is designated 23E3.

The ilvG2096 (Val$^r$) mutation (Lawther et al., *Proc. Natl. Acad. Sci. USA*, 78: 922–925 (1981)) was introduced by homogenotization. This mutation repairs a frameshift that causes the wild-type *E. coli* K-12 to be sensitive to valine. Strain 23E3 was transformed with plasmid pAH29 (Lawther et al., supra) containing the ilvG2096 (Val$^r$) marker and an ampicillin-resistance gene. A strain designated 33B6, which had spontaneously lost the plasmid and which had acquired the desired allele, was identified by screening ampicillin-sensitive clones for valine resistance.

Finally, two mutations in the carbohydrate-utilization pathway were introduced to allow this host to be distinguished from other recombinant hosts by a simple carbohydrate utilization test. Deletion mutations of fucP and malE were constructed by PCR and were separately incorporated into a plasmid vector containing beta-lactamase and levan sucrase (Bass et al., supra). Each entire plasmid was recombined into the chromosome of a W3110 derivative that would not support independent replication of the plasmid vector (Bass et al., supra). Strain 33B6 was then transduced to carbenicillin resistance with P1 phage grown on the W3110 derivative carrying the fucP deletion plasmid integrated into its chromosome. Derivatives no longer expressing levan sucrase and therefore sucrose resistant were selected and screened for loss of carbenicillin resistance and inability to use fucose. The resulting strain, 49B2, was confirmed to carry the planned fucP deletion using PCR.

These steps were repeated to incorporate the malE deletion. Strain 49B2 was transduced to carbenicillin resistance using P1 phage, and grown on the strain carrying the malE deletion plasmid integrated into its chromosome. Then sucrose-resistant derivatives were selected and screened for loss of carbenicillin resistance and inability to use maltose, and the presence of the malE deletion was confirmed by PCR.

The important characteristics of the strain 49A5 include the following:

It is resistant to T1 phage.

It does not overproduce alkaline phosphatase, when phosphate is depleted (which is the condition used to induce product synthesis).

It lacks a protease.

It is not susceptible to valine toxicity.

It can be distinguished from other hosts by a carbohydrate-utilization test.

2. Strain 58B3

The strain 58B3 was also derived from the 33B6 strain. The Δprc:pS1080 genotype (Bass et al., supra; Metcalf et al,

*Gene*, 138: 1–720 (1994)) was introduced into a kan$^s$ derivative of strain 33B6 (56G4) by P1 transduction, selecting for colonies not growing well on half-strength LB with low salt at 42° C. The kan$^s$ strain carries the degP deletion derived from pKS16 (Strauch and Beckwith, 1989, supra), resulting in a kanamycin-sensitive phenotype. Therefore, 58B3 strain is a kan$^s$ strain carrying both degP and prc deletion.

The complete genotype of 58B3 strain is W3110 ΔfhuA phoAΔE15 Δ(argF-lac)169 deoC degP41 IN(rrD-rrE)1 Kan$^s$ ilvG2096(Val$^r$) Δprc.

3. Strain 59A7

This strain is constructed by introducing the Prc suppressor (Spr mutant) into the 58B3 strain. The P1 phage lysate of the 51B9 strain (tonA prc prc sup zeg722::Tn10) was transduced into the 58B3 strain selecting for tet-resistant colonies and screening for the Prc suppressor phenotype (growing well on half-strength LB with low salt at 42° C.). The new strain is called 58F1. The Δprc mutant cannot survive at 42° C. The tetracycline-resistance gene was removed from 58F1 by plating on Malloy plates, which resulted in a tet$^s$-sensitive strain, designated 59A7. The complete genotype of the 59A7 strain is W3110 ΔfhuA phoAΔE15 Δ(argF-lac)169 deoC degP41IN(rrD-rrE)1 Kan$^s$ ilvG2096(Val$^r$) Δprc sprW148R.

The original 51B9 strain has a Prc suppressor Spr, which carried a point mutation W148R, the same as Spr in the 43H1 and 59A7 strains.

4. Strain 43H1

The complete genotype of the 43H1 strain is very similar to that of 49A5: W3110 ΔfhuA phoAΔE15 Δ(argF-lac) 169 degP41(Δpst1-Kan$^r$) IN(rrD-rrE)1 ilvG2096(Val$^r$) ptr3 ΔompT prc::kanr sprW148R. It carries three more protease markers than 49A5, Ptr3 OmpT and Prc. This strain has the point mutation (W148R) in the Spr. It is Kan$^r$.

5. Strain 58H2

The 43H1 strain was transduced to tet$^r$ with P1 phage grown on strain 42E3. This strain (58F9) was repaired for the prc::kan$^r$ mutation; therefore, it became kan$^s$. This strain was then plated on minimal glucuronic acid medium to remove the eda::Tn10. The new strain created, 58H2, is kan$^s$ and became a triple-protease mutant with wild-type prc. The complete genotype of the 58H2 strain is W3110 ΔfhuA phoAΔE15 Δ(argF-lac)169 degP41(Δpst1-Kan$^r$) IN(rrD-rrE)1 ilvG2096(Val$^r$) ptr3 ΔompT sprW148R.

6. Strain 45F8

The complete genotype of the 45F8 strain is W3110 ΔfhuA Δ(argF-lac)169 degP41 Kan$^s$ ΔompT ptr3 ilvG2096 (Val$^r$) phoS*(T104). This is aphoS strain with triple-protease markers.

7. Strain 41H1

The complete genotype of the 41H1 strain is W3110 ΔfhuA phoS* (T104) Δ(argF-lac)169 degP41 (Δpst1-Kan$^r$) ptr3 ilvG2096(Val$^r$) T-adapted at 37° C. This is a phoS strain with dual-protease markers.

8. Strain 33D3

The complete genotype of the 33D3 strain is W3110 ΔfhuA ptr3 lacIq lacL8 ΔompT degP41 (ΔpstI-kan$^R$). A description of the construction can be found, e.g., in U.S. Pat. No. 5,789,199.

K. Shake Flask and Fermentation Cultures

For the shake-flask experiment, Luria-Bertani (LB) broth and C.R.A.P. minimal medium were used with 5 μg/mL of AMPICILLINE™ antibiotic. The C.R.A.P. minimal medium was prepared as follows: 3.57 g (NH$_4$)$_2$SO$_4$, 0.71 g NaCitrate-2H$_2$O, 1.07 g KCl, 5.36 g yeast extract, and 5.36 g TM HYCASE SF-SHEFFIELD™ were mixed, the pH was adjusted with KOH to 7.3, and the volume was adjusted to 872 mL with deionized water. This mixture was then autoclaved and cooled to 55° C. 110 mL 1 M MOPS buffer at pH 7.3, 11 mL 50% glucose, and 7.0 mL 1 M $MgSO_4$ were added.

The *E. coli* fermentation process employed herein was a high-cell-density process as defined above. To reach higher cell densities, ammonia was added continuously, and additional minor nutrients (P, K, S, and Mg) were added at certain stages of the fermentation to support cell growth. Lowering the amount of nutrients resulted in another process having lower final optical density of the broth with equal quality of product, which is referred to herein as the low-cell-density process.

A single vial containing 1.5 mL of culture in 10–15% DMSO was thawed into a 1-L shake flask containing 500 mL of LB medium supplemented with 0.5 mL of tetracycline solution (5 mg/mL) and 2.5 mL 1M sodium phosphate solution. This seed culture was grown for approximately 16 hours at 30° C. and was then used to inoculate a 10-liter fermentor.

The fermentor initially started with approximately 6.5 L medium containing about 4.4 g glucose, 100 mL 1M magnesium sulfate, 10 mL of a trace element solution (100 mL hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, and 5 g manganese sulfate monohydrate, in a final volume of 1 liter), 20 mL of a tetracycline solution (5 mg/mL in ethanol), 10 mL of FERMAX ADJUVANT 27™ (or some equivalent anti-foam), 1 bag of HCD salts (37.5 g ammonium sulfate, 19.5 g potassium phosphate dibasic, 9.75 g sodium phosphate monobasic dihydrate, 7.5 g sodium citrate dihydrate, and 11.3 g potassium phosphate monobasic), and 200 g NZ Amine A (a protein hydrolysate). Fermentations were performed at 30° C. with 10 slpm of air flow and were controlled at a pH of 7.0±0.2 (although occasional excursions beyond this range occurred in some cases). The back pressure of the fermentor and agitation rate were varied to manipulate the oxygen transfer rate in the fermentor, and, consequently, to control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Further additions of anti-foam were also used in some cases to control foaming. When the culture reached a cell density of approximately 40 OD550, an additional 100 mL of 1M magnesium sulfate was added to the fermentor. Additionally, a concentrated salt feed (consisting of approximately 10 g ammonium sulfate, 26 g dibasic potassium phosphate, 13 g monobasic sodium phosphate dihydrate, 2 g sodium citrate dihydrate and 15 g monobasic potassium phosphate in 1 L of water) to the fermentor was started at a rate of 2.5 mL/min when the culture reached approximately 20 OD550 and continued until approximately 1250 mL were added to the fermentation. Fermentations were typically continued for 72–80 hours.

During the fermentation, once the dissolved oxygen setpoint for the fermentation was reached, the concentrated glucose solution was fed based on the dissolved oxygen probe signal to control the dissolved oxygen concentration at the setpoint. Consequently, in this control scheme, manipulations of fermentor-operating parameters such as the agitation rate or back pressure, which affect the oxygen transfer capacity in the fermentation, correspondingly manipulated the oxygen uptake rate or metabolic rate of the cells.

A mass spectrometer was used to monitor the composition of the off-gas from the fermentation and enabled the calculation of the oxygen uptake and carbon dioxide evolution rates in the fermentation.

When the culture reached a cell density of approximately 220 OD550, the agitation was decreased from an initial rate of 1000 rpm to approximately 725 rpm over approximately 12 hours.

For fermentation of cells transformed with pMS421 and pcyc34 (where the tacII promoter was used to control both heavy- and light-chain expression), or of cells transformed with pMS421 and the dual-promoter plasmid pxCD18-7T3 (where the tacII promoter was used to control heavy-chain expression), 50 mL of 200 mM IPTG was added approximately 12 hours after the culture reached a cell density of 220 OD550 to induce heavy- and light-chain synthesis for pcyc34 and heavy-chain synthesis for pxCD18-7T3.

Results

A. The Kappa-Light-Chain Cleavage Products Discovered and Identified

Soluble *E. coli* extracts (see HSE in Materials & Methods) and the remaining pellets, suspended in SDS sample buffer (a commonly available commercial product for running a SDS gel) were analyzed by SDS-PAGE. The samples were derived from the 20 OD-mL pellets collected during the *E. coli* high-cell-density (HCD) fermentation in the 49A5 strain carrying the pS1130 plasmid for rhuF(ab)'2LZ (xCD18) production. In the soluble fraction the kappa LC cleavage fragment, 115 amino acids in length, was identified. In the insoluble fraction the kappa LC cleavage fragment, 182 amino acids in length, was identified. All the fragments were transferred to a PVDF membrane and sequenced. Both of them had the correct N-terminus as the processed forms of kappa-LC. The masses were determined by mass spectrometric analysis to be 12488.5 and 19857.2 Da, respectively. The sites of proteolytic cleavage were between residues Val 115 and Phe 116 for LC-115 and between residues Ser182 and Lys183 for LC-182. Only one site looked like a typical Prc clipping site.

Another *E. coli* 20 OD-mL pellet at the end of this fermentation was analyzed by two-dimensional gel electrophoresis. *E. coli* cell lysate of the pellet (~40 μg protein) was combined with rehydration solution as described by Champion et al, supra. On the 2-D gel pattern of cells derived from the 49A5/pS1130 fermentation, the kappa-light-chain-specific spots were identified by comparing the production gel with a blank 2-D gel derived from cell pellets of a (49A5/pBR322) fermentation at a similar time point. The pellets were chosen from the same time point of two fermentations, assuming the cells should be in comparable metabolic states. All the kappa LC spots were identified by immunoblot using alkaline-phosphatase-conjugated anti-human kappa LC antibody.

Figure 6:
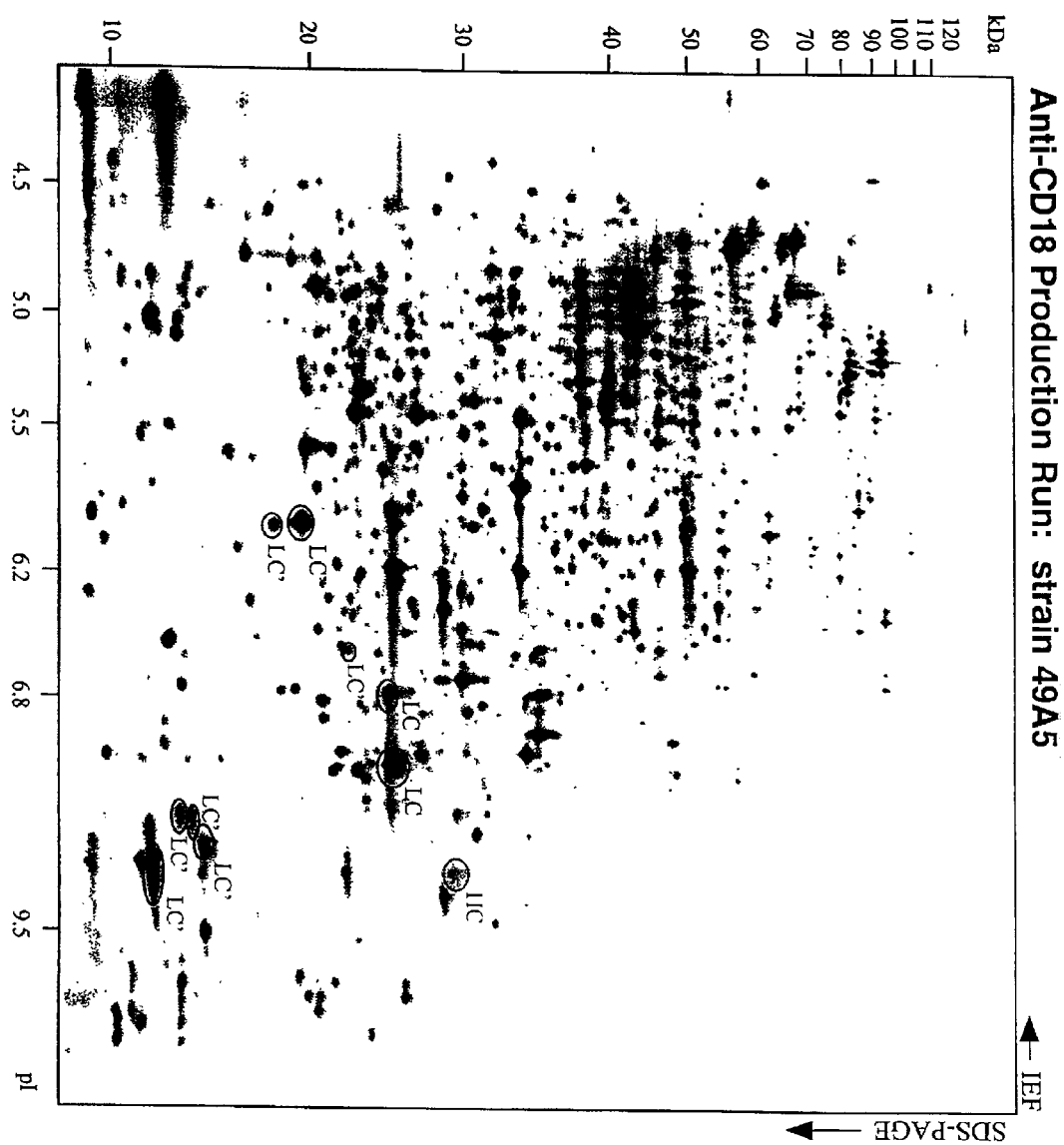
FIG. 6 depicts the 2-D gel result of the fermentation cell pellet derived from strain 49A5 (prc-plus strain), expressing the rhuFab'2 anti-CD18-LZ fusion as a heterologous polypeptide. All the LC-related spots are circled.

Besides the two major clips identified by 1-D gel analysis, the 2-D gel showed intact LC, an iso-form of intact LC, and at least 5 more minor LC-clips (see FIG. 6). The corresponding spots were eluted and sequenced. All the LC-specific peptides had the correct N-terminus, indicating that they are all well processed with the STII signal being cleaved. All of these peptides were analyzed by mass spectrometer to measure the approximate mass. Due to the trace amount of the minor clips present, a correct mass could not be obtained to determine the clipping sites of those fragments.

Three minor clips clustered with the Kappa LC-115 clip at pI value around 9. The fourth one had a pI value around 6.5 and the fifth one had the same pI value as the LC-182 clip at pI around 6. To decide the solubility of these LC fragments, a HSE of an identical pellet was loaded on a 2-D gel. The $LC_{182}$ fragment only existed in the insoluble fraction.

B. Prc is the Sole Protease Responsible for the Cleavage of Kappa Light Chain

1-D SDS-PAGE gels loaded with the insoluble fraction of cells derived from four different fermentations of *E. coli* protease mutants, 49A5, 45F8, 41H1, and 431H1, expressing anti-CD18 Fab'2 LZ molecule were compared. The LC-182 proteolytic cleavage was present in three of the four samples (not in the prc-deletion strain 43H1), indicating that the Prc protease might be involved in kappa-LC cleavage. Peak 1, which corresponds to the LC-115 clip, present in samples derived from strain 49A5 (prc-plus), also disappeared from the 43H1-derived samples when comparing chromatograms resolved by the AME5™/RP dual-column assay. This assay selectively adsorbed kappa-LC-containing antibody species and then resolved them into five peaks as described above in the Material and Methods section.

Figure 7:
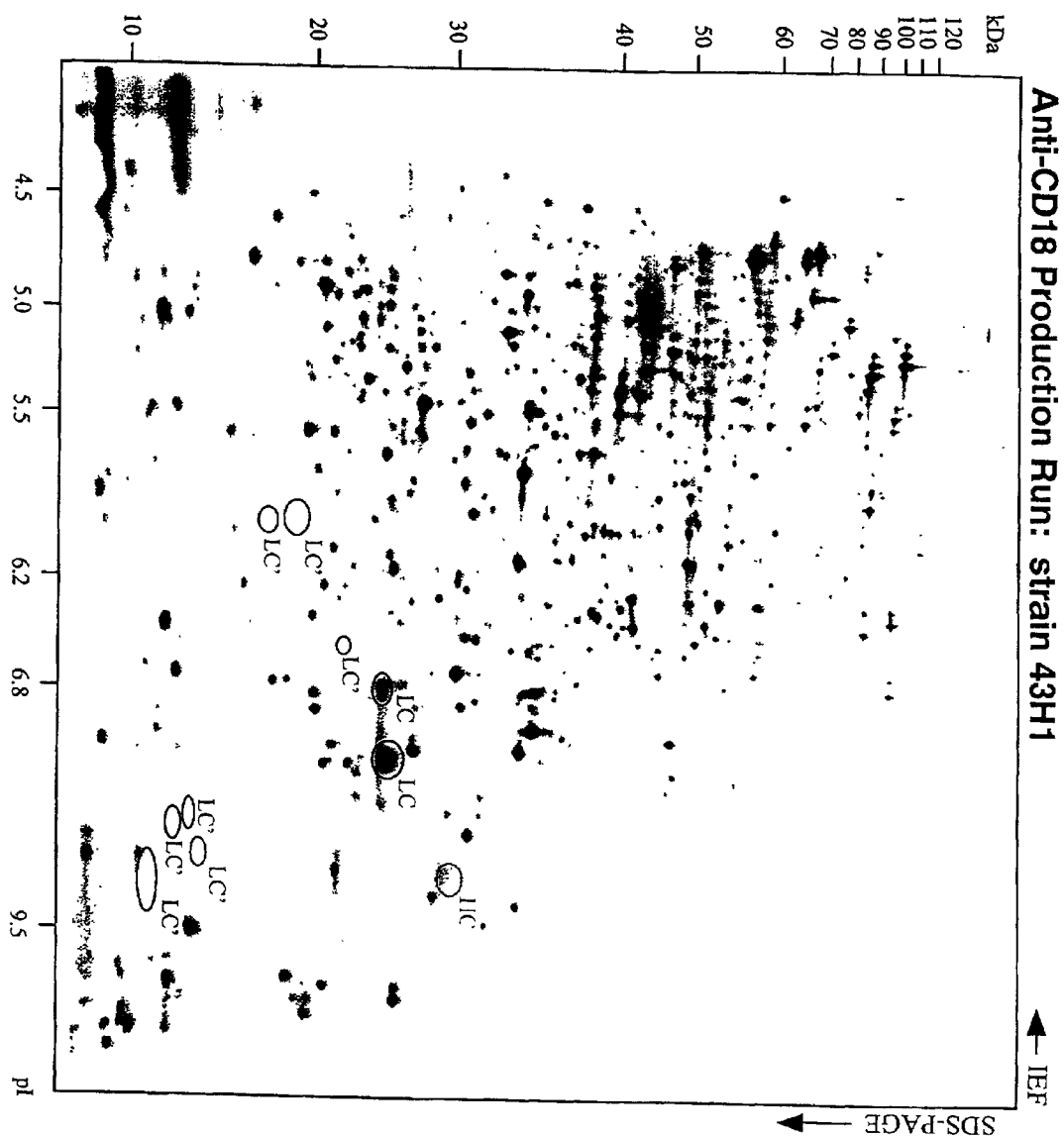
FIG. 7 depicts the 2-D gel result of the fermentation cell pellet derived from strain 43H1 (prc-minus strain), expressing the rhuFab'2 anti-CD18-LZ fusion as a heterologous polypeptide. In this gel the LC-cleavage products disappear.

When the 2-D gel of 43H1-derived cell pellets was analyzed, it was found that not only LC-115 and LC-182 fragments disappeared from the gel, but also all the other LC-related minor species disappeared (see FIG. 7). This result strongly suggests that Prc is the only enzyme responsible for kappa-LC cleavages. This 43H1 cell pellet was derived from a low-cell-density fermentation.

C. Strain Construction to Confirm that Prc is the Only Enzyme Involved in Kappa-Light-Chain Cleavage 1. A prc-deletion Strain to Become prc-plus Proof that Prc is the only enzyme involved in kappa-LC cleavage was obtained by repairing the 43H1 strain (a prc-minus host with quadruple protease markers) to become a prc-plus, triple-protease strain (58H2). A strain 42E3 carries eda-51::Tn10, which is cotransducible with prc. The 43H1 strain was transduced to tet$^r$ with P1 phage grown on 42E3. The resulting strain (58F9) was repaired for the prc::kan$^r$ mutation; therefore, it became kan$^s$. This strain was then plated on minimal glucuronic acid medium to remove the eda::Tn10. The new strain created, 58H2, became a triple-protease mutant with wild-type prc. This isolate is either a transductant or spontaneous Eda$^+$ isolate. The prc-plus genotype was confirmed by PCR. This 58H2 strain still carries the prc suppressor (spr$^{W148R}$) derived from 43H1, and it is kan$^s$. The re-appearance of LC-clips in this 58H2 strain was detected by the AME5™/RP dual-column assay (see FIG. 8).

2. The prc Gene was Deleted from a Native Strain to Become prc-minus

The strain 49A5 was a prc wild-type strain, as described above. When the prc deletion was introduced into this strain background to construct the 58B3 strain and the cell extracts were assayed by the AME5™/RP dual-column method, the LC-115 clip (peak 1) disappeared. The strain 58B3 was derived from the 33B6 strain, which carries only a protease marker, DegP. The Δprc::pS1080 (Bass et al., supra; Metcalf et al., supra) was introduced into a kan$^s$ derivative of 33B6 (56G4) by P1 transduction to create a degP Δprc dual-protease strain, 59A7.

A summary of the cleavage results for all seven strains is shown in Table 1.

TABLE 1

*E. coli* Host Strains Expressing anti-CD18 F(ab)'2 Leucine Zipper

| *E. coli* host | Protease marker | LC degradation |
|---|---|---|
| 49A5 | DegP | + |
| 45F8 | DegP Ptr3 | + |
| 41H1 | DegP Ptr3 OmpT | + |
| 43H1 | DegP Ptr3 OmpT ΔPrc Spr$^{W148R}$ | − |
| 58H2 | DegP Ptr3 OmpT Spr$^{W148R}$ | + |
| 58B3 | DegP ΔPrc | − |
| 59A7 | DegP ΔPrc Spr$^{W148R}$ | − |

D. Yield Improvement of rhuFab'2 LZ (xCD18) in prc-Minus Hosts

1. Shake Flask Results

Three strains (49A5, 43H1, and 58H2) expressing rhuFab'2 LZ (xCD18) were first grown in LB broth +Amp overnight at 30° C. Then all the cultures were equally inoculated into shake flasks containing 25 mL of the C.R.A.P. minimal medium +Amp and continued to shake overnight at 30° C. Twenty OD-mL pellets were collected to make the soluble lysates (HSE). Twenty-five $\mu$l out of 530 $\mu$l was loaded into the AME5™/Reverse-Phase columns.

Figure 8:
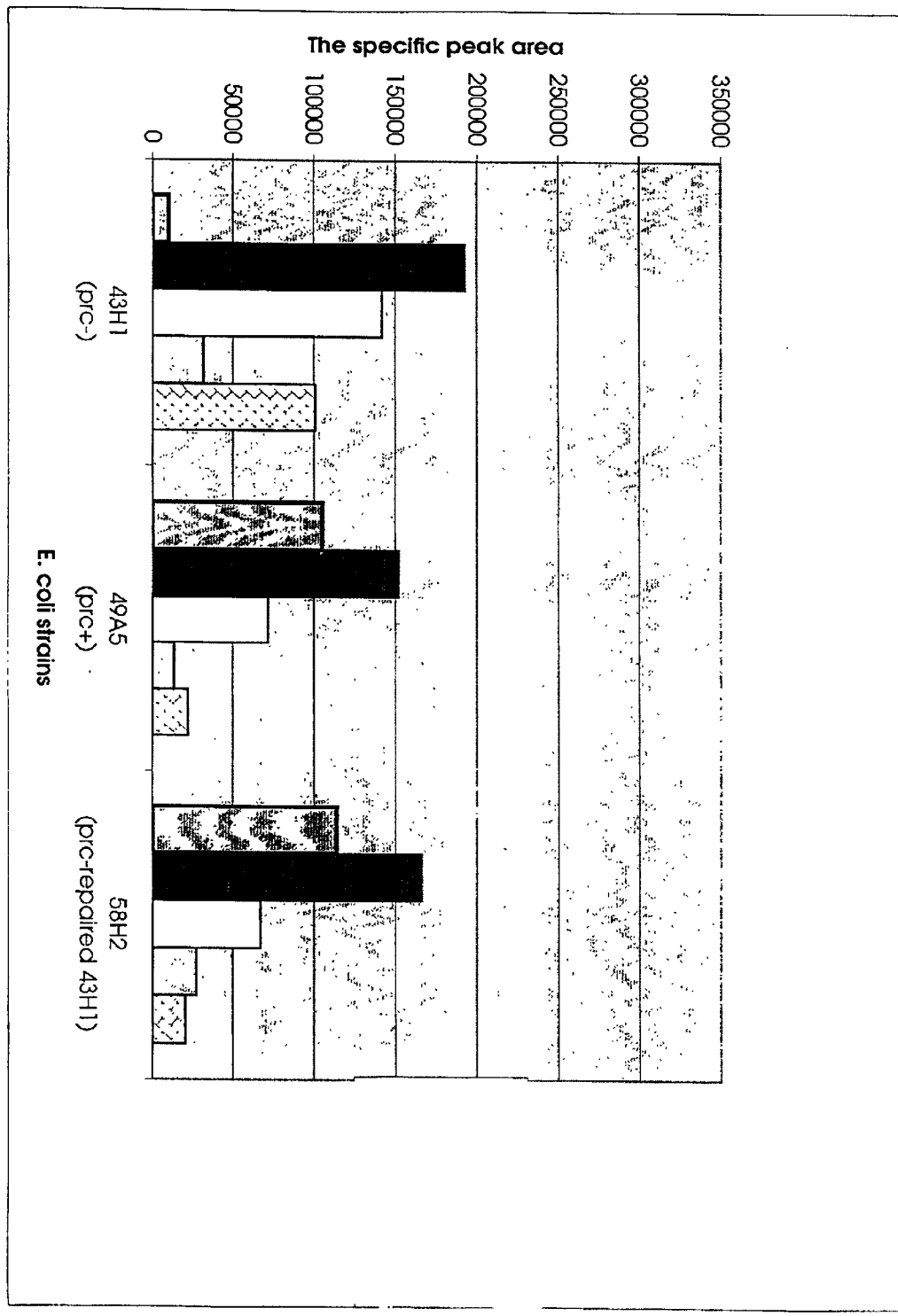
FIG. 8 shows the five peaks resolved by an assay using AME5™/Reverse-Phase columns and thereby provides a comparison of the partition of rhuFab'2 LZ (xCD18) antibody fragments thus resolved. The y-axis is the specific peak area of peaks 1 to 5. The x-axis shows the three rhuFab'2 LZ (xCD18) production strains, 43H1 (prc−), 49A5 (prc+), and 58H2 (prc-repaired 43H1). The gray with thick border bar is LC-115; the black bar is LC, the white bar is LC dimer, the gray with thin border bar is Fab-like molecule, and the brick-like pattern bar is Fab'2-LZ. It can be seen that peak 1 (LC-115) disappeared from the prc-deletion strain.

FIG. 8 shows the bar graph representing the five peaks resolved by this assay. The Y-axis is the specific peak area of peak 1 to 5 (see Materials & Methods). The X-axis shows the rhuFab'2 LZ (xCD18) production strains. Both prc+ strains, 49A5 and 58H2, produced almost equal amounts of product, and both of them showed almost equal amounts of LC-115 fragment (peak 1), compared to almost nothing in peak 1 and more peak 5 product in the Δprc strain (43H1). This graph showed the partition of antibody fragments. Higher amounts of soluble, intact LC and LC dimer were observed in the 43H1 host than in the 49A5 and 58H2 hosts. In shake flasks the prc− host produced almost 5-fold more of the rhuFab'2 LZ (xCD 18) product than did the native prc strains.

2. Fermentation Results

The average rhuFab'2 LZ (xCD18) titer obtained by the standard high-cell-density (HCD) fermentation was 893 mg/L in the wild-type prc host (49A5, n=6), based on the AME5™/RP dual-column assay. A close to two-fold titer improvement was observed from the 43H1/pS1130 fermentation. The dramatic difference between the shake flask (5x) and fermentation (<or equal to 2x) titers for the 43H1 and 49A5 hosts, respectively, was, without being limited to any one theory, probably due to the difference in secretion efficiency of products. When the total lysates of shake-flask pellets were analyzed, only 50% of the antibody fragments were correctly processed in the prc-plus background, while the lysate derived from 43H1 shake-flask cells or all the fermentation-derived cells (prc-plus and minus) showed 100% processing. The processing of Prc protein was found to be secY, secA dependent (Hara et al.,1991, supra). Without being limited to any one theory, it is believed that the shake flask result shows that the Prc protein competed with the antibody fragments for translocation.

3. Total Expression of Antibody Fragments was Measured

A POROS™ column assay of whole broth fermentation samples was developed as described in the Materials & Methods section, to assess the efficiency of antibody folding and assembly. When equal injections of whole broth samples derived from three anti-CD18HCD fermentations were compared in different hosts, it was found that the 43H1 fermentation expressed a similar amount of HC as the 49A5 fermentation, but a higher amount of intact kappa-LC (see Table 2). The rhuFab'2 LZ (xCD18) titer was 1830 mg/L for 43H1 compared to 887.8 mg/L for 49A5. The 59A7 fermentation not only produced extra antibody fragments, it also resulted in the highest titer of rhuFab'2 LZ (xCD18) at 2403 mg/L.

TABLE 2

The Total Expression of Antibody Fragments and the Fab'2-LZ Titers of Different Strains Expressing rhuFab'2LZ (xCD18) by Standard HCD Fermentation Process

| Fermentation Samples | Host | Total LC (g/L) | Total HC (g/L) | Total HC + LC (g/L) | Fab'2-LZ (mg/L) | Time (hr) |
|---|---|---|---|---|---|---|
| 1 | 49A5 | 2.23 | 2.27 | 4.5 | | 40 |
| 2 | " | 4.75 | 3.96 | 8.71 | 887.8 | 72 |
| 3 | 43H1 | 6.57 | 4 | 10.57 | | 62 |
| 4 | " | 7.38 | 4.18 | 11.56 | 1830 | 72 |
| 5 | 59A7 | 12.49 | 6.87 | 19.36 | | 68 |
| 6 | " | 13.76 | 7.46 | 21.22 | 2403 | 72 |

E. Prc Suppressor is Required for Stationary Phase Survival

Figure 9:
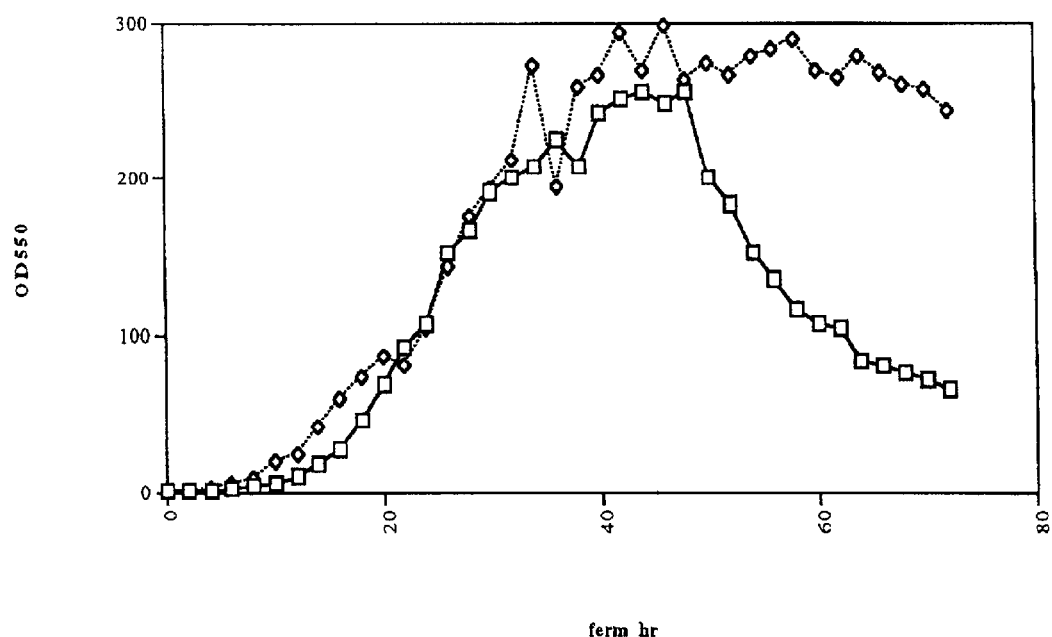
FIG. 9 shows the growth profiles of standard high-cell density fermentation in prc-minus without a mutant spr gene (58B3 transformed with pS 1130) (squares) and prc-minus with a mutant spr gene (59A7 transformed with pS1130) (diamonds) strains, expressed as OD550 as a function of fermentation hours.

It was found that the 58B3 strain, carrying the degP and prc deletions, exhibited lysis during the prolonged stationary phase growth of a HCD fermentation expressing anti-CD18 Fab'2 LZ molecule. The cell lysis started at 50 hrs after inoculation. It produced only 320 mg/L of rhuFab'2LZ (xCD18), while the 59A7/pS1130 fermentation maintained good growth at stationary phase until 72 hrs of a HCD fermentation to reach high cell density (about 300 $OD_{550}$-mL). FIG. 9 shows the growth comparison of these two fermentations. Also found was extra high expression of both the HC and LC fragments in this strain background, which increased the yield of the rhuFab'2 LZ (xCD18) molecule to 2403 mg/L. Again no kappa-LC clips were found in samples derived from both 58B3 and 59A7 prc-deletion strains.

The prc suppressor (spr) (encoding $Prc^{sup}$) was originally isolated herein from strain 40A6 (prc::kan spr), as a spontaneous mutation, i.e., a thermoresistant revertant of the prc deletion mutant. After the gene was sequenced and conjugation mapped, it was found to be located at approximately 48 min on the E. coli chromosome. The nucleotide sequence of its PCR product matched that of the E. coli spr gene reported by Hara et al., 1996, supra, except for one point mutation at amino acid 148, in which a TGG codon was changed to CGG, which resulted in a change of a tryptophan residue into arginine (W148R). This prc suppressor when introduced into the 59A7 strain had the W148R mutation. The wild-type spr gene was reported to encode a lipoprotein in the envelope fraction, which is suspected to be a peptidoglycan-hydrolyzing enzyme (Hara et al., 1996, supra).

The Prc suppressor was introduced into the 59A7 strain by a Tn10 linked to this suppressor, and co-transductants were selected for that are both tetracycline resistant and capable of growing on a half-strength LB low-salt plate at 42° C. The new point mutation occurred at the time when Tn10 was removed by Malloy plates.

Based on the anti-CD18 Fab'2 fermentation results of 58B3 versus 59A7 strains, the Prc suppressor was shown to be required for successful growth of a ΔPrc mutant, especially in a high-cell-density E. coli fermentation. The strain, designated as 58B3, carries exactly the same genotype as 59A7 except for spr (W148R), and could not stay viable in a standard HCD fermentation after 50 hours.

F. The Prc Deletion Mutant can Increase Various Antibody Production Levels due to the Location of the Prc Clipping Sites FIG. 10 shows the humanized kappa LC sequence (SEQ ID NO:5). The calculated pI values of potential Prc clips are shown in Table 3.

TABLE 3

Calculated pI. Values of Potential Prc Clips

| calculated PI value | cleavage site | protease type | LC-clips |
|---|---|---|---|
| 5.97 | S/K | Serine specific | LC-182 |
| 9.14 | V/F | prc | LC-115 |
| 9.14 | S/V | Serine specific | LC-114 |
| 9.14 | V/A | prc | LC-110 |

Without being limited to any one theory, based on FIG. 10 and Table 3 it is believed that the Prc protease started to clip the kappa-LC from its C-terminus, 9 or 18 amino acids into the LC sequence, and then gradually chewed it toward the N-terminus to open up the S/K site for a serine-specific protease to work. It was possible that another kappa LC species (possibly in a different folding state) got cleaved mainly up to 115 amino acids. Many potential cleavage products have molecular weights and calculated pI values that are matched quite well with the kappa LC spots found from the 2-D gel.

Figure 11:
FIG. 11 depicts a gel with seven lanes using different hosts and three types of proteins. This gel shows that the 20-kD LC clip ($LC_{182}$) is not present in 43H1 (prc−) cells expressing anti-VEGF Fab and anti-tissue factor Fab'2-LZ fusion molecules. Lane 1 is anti-tissue factor F(ab')2 LZ 6× His, host strain 33B6, lane 2 is anti-tissue factor F(ab')2 LZ 6× His, host strain 43H1, lane 3 is anti-CD18 F(ab')2 LZ 6× His, host strain 49A5, lane 4 is anti-CD18 F(ab')2 LZ 6× His, host strain 41H1, lane 5 is pBR322, host strain 49A5, lane 6 is anti-VEGF Fab, host strain 43H1, and lane 7 is anti-VEGF Fab, host strain 43E7. The designations HC and H represent heavy chain, and LC and L represent light chain.

FIG. 11 shows that the prc-deletion strain (43H1) eliminated the LC-182 clip from cells expressing anti-VEGF Fab, anti-CD18 Fab'2 LZ, anti-CD18 Fab'2-LZ-6xHis molecules and anti-tissue factor Fab'2-LZ-6xHis molecules. The fermentation samples derived from cab2826 (33B6/D3H44-F (ab')2) and cab2847 (43H1/D3H44-F(ab')2) were high-cell density fermentations intended to express the anti-tissue factor Fab'2 LZ-6xhis molecule. The fermentation process was the same standard HCD process as described above for anti-CD18 Fab'2 LZ fermentations. Cab2793 was the 49A5/pAB3 fermentation intended to express the anti-CD18 Fab'2 LZ-6xHis molecule. Cab 2846 was the 41H1/pS1130 fermentation intended to express anti-CD18 Fab'2 LZ molecule. JJ81 (43H1/pY0317) and JJ67 (43E7/pY0317) fermentations were intended for making anti-VEGF Fab. Cab 2814 was (49A5/pBR322), blank fermentation, which contains the similar plasmid backbone without antibody-expressing genes.

The 20-OD fermentation pellets were extracted with TRIS/EDTA/lysozyme to remove the soluble HSEs. The remaining pellets were suspended in 400 μL of 1× SDS sample buffer plus 20 μL of beta-mercaptoethanol, and then were heated at 95° C. on a heat block for 5 minutes. Then 5 μl was loaded into the 4–12% NUPAGE™ gel. The 33B6, 41H1, 49A5, and 43E7 strains are prc-plus strains. The 43H1 strain was a prc-minus strain. All the native prc-strain-derived samples have the 19.8-kD LC degraded product. The cab2829 (33B6/pD3H44TB) fermentation sample, which expressed anti-TF Fab, could also detect the same size LC-degradation fragment. All of these fragments were amino acid sequenced and found to have their correct N-terminal LC sequences.

G. Strain 59A7 Shows Superior Expression in Shake Flasks for anti-CD18His- and Lys-Tagged Fab'2 LZ and Apo2L Cytoplasmic Protein Additional shake flask data shown in Table 4 indicate that the strain 59A7 expressed pAB3 (the anti-CD18His-tagged Fab'2 LZ) better than did the strain 43H1 and 49A5. The strain 59A7 expressed pAB21 (Lys-tagged Fab'2 LZ) better than did the 33B6 strain by 2.4 fold. The strains 59A7 and 43H 1 expressed pS 1130 (Fab'2 LZ without tag) better than the 49A5 strain by 2.9 fold. However, fermentation results always showed that strain 59A7 is better than strain 43H 1 in pS 1130 expression.

For the non-antibody cytoplasmic protein Apo2L, the specific activity is about 20–30% higher when expressed in strain 59A7 than in strain 43E7 (in shake flasks). Since strain 43E7 grew to a higher OD550, the total expression was similar. The 43E7 strain is an ompTptr3 degP strain without prc and spr.

TABLE 4

The Higher Specific Titers of Various Proteins Expressed in 59A7 and Other Strains in Shake Flask Cultures

| Strain | Protease marker(s) | pS1130 mg/L/OD-mL | pAB3 mg/L/OD-mL | pAB21 mg/L/OD-mL | Apo2L mg/L/OD-mL |
|---|---|---|---|---|---|
| 33B6 | DegP | N.A. | N.A. | 0.33 | N.A. |
| 49A5 | DegP | 0.38 | 0.46 | N.A. | N.A. |
| 43H1 | DegP Ptr3 OmpT Prc Spr$^{W148R}$ | 1.1 | 0.3 | N.A. | N.A. |
| 59A7 | DegP Spr$^{W148R}$ | 1.1 | 0.7 | 0.8 | 14.4 |
|  |  |  |  |  | 15.2 |
| 43E7 | DegP Ptr3 OmpT | N.A. | N.A. | N.A. | 12.2 |
|  |  |  |  |  | 11.4 |

H. Strain 59A7 Shows Superior Expression by Fermentation for anti-CD18 Fab'2 LZ

Table 5 indicates that strain 59A7 was superior to 33D3 in expressing anti-CD18 Fab'2 LZ from the dual-promoter plasmid pxCD 18-7T3 and superior to 49A5 in expressing anti-CD 18 Fab'2 LZ from plasmid pcyc34.

TABLE 5

The Higher Specific Titers of Anti-CD18 Fab'2 LZ Expressed in 59A7 as Compared to 33D3 and 49A5 Using Two Different Plasmids By Fermentation

| Strain | Plasmids | anti-CD18 Fab'2 LZ Titer by CSX Assay (mg/L) (Average) |
|---|---|---|
| 33D3 | pxCD18-7T3/pMS421 | 2500 |
| 59A7 | pxCD18-7T3/pMS421 | 4000 |
| 49A5 | pcyc34/pMS421 | 341.3 |
| 59A7 | pcyc34/pMS421 | 2067.1 |

Discussion

In this work, the degradation of the kappa-LC in *E. coli* cells expressing anti-CD18 Fab'2-LZ molecule was investigated. Previous studies have shown many potential Prc substrates, but as best as can be ascertained, no one has reported the finding of antibody fragments as the substrate of this protease. Here it is shown that Prc is the only protease involved in kappa LC cleavage inside *E. coli* cells. The Prc protein appeared to cleave kappa-LC selectively at discrete sites, which resulted in two major clips (LC-115 & LC-182) and five extra minor cleavage products, as observed from the 2-D gel results. Since one of the major clips was a S/K cleavage product, which did not fit the characteristics of Prc clipping sites (Keiler et al., supra), it was investigated more fully. It has now been found that the degradation of kappa light chain in *E. coli* cells relates to an *E. coli* periplasmic protease (Prc/Tsp). Kappa light-chain-cleaved products were identified by analytical methods (1-D/2-D SDS PAGE, mass spectrometry, and N-terminal sequencing analysis) of *E. coli* extracts derived from various proteolytically-deficient strains expressing anti-CD18 F(ab)'2 leucine zipper molecule, to confirm that Prc/Tsp is the sole protease responsible for kappa light-chain cleavage.

The special combination of degP prc deletion with a prc suppressor (spr mutant) is found to be a unique *E. coli* strain capable of producing very high amounts of recombinant protein or higher specific activity of the protein, as exemplified herein by Apo2 ligand and active antibody.

Fermentation using the degP prc spr strain herein results in high cell-density growth (to 300 OD or more) and in production of high yields of rhuxCD18 Fab'2 leucine zipper product compared with the expression of antibodies in the wild-type strain or other proteolytically-deficient strains.

The fermentation process herein allows the production of 100–200 g/L of cell dry weight in 72 hours with a greater than 200% increase in active antibody produced in one preferred strain 59A7, having the combination degP prc spr. The complete genotype of the 59A7 strain is W3110 ΔfhuA phoa ΔE15 Δ(argF-lac)169 deoC degP41 IN(rrD-rrE)1 kan$^s$ ilvG2096(Val$^r$) Δprc spr$^{W148R}$. Its parent strain is 58B3, which has identical genetic markers as the 59A7 strain except without the prc suppressor, spr. The 58B3 strain was unable to sustain growth in the stationery phase of an *E. coli* high-cell-density fermentation process. It produced lower antibody product than a native prc strain (49A5), which also carries the degP deletion marker and other identical genotypes as the 59A7 strain, except that 49A5 is a kanamycin-resistant prc native strain, while 59A7 is a kanamycin-sensitive Δprc strain.

Hence, it has been hereby discovered that the presence of the prc suppressor (spr) is essential for good growth and a high level of antibody production in a degP prc deletion strain, especially in a high-cell-density fermentation process, but also in a low-cell density fermentation process.

A DegPΔ single-protease mutant and other multiple-protease-deficient strains that included degPΔ did not produce an extra high level of recombinant products. The two strains mentioned earlier, degP rpoH and degP prc, expressed more product than many other strains to which they were compared, but not nearly as much as did the 59A7 strain. More specifically, without the spr suppressor, the strain 58B3 with the degP prc combination did not show any benefit in producing antibody fragments, as exemplified by the anti-CD18 Fab'2 LZ molecule.

Analytical results are provided to prove that the cleavage of kappa LC in *E. coli* cells expressing humanized anti-CD 18 F(ab)'2-leucine zipper molecule relates to the periplasmic C-terminal processing protein (Prc). The Prc protein is the sole protease responsible for the cleavage of kappa light chain, which was proved by both two-dimensional gel electrophoresis and by genetic manipulation of the antibody production strains. To confirm that the Prc protease is truly the only enzyme involved in kappa LC cleavages, when a Δprc strain was repaired into a native prc strain, the kappa LC-cleaved products reappeared. Similarly, when the prc gene was deleted from a native prc strain, the LC-cleaved products disappeared. Both strain constructions were performed by P1 transduction.

Additionally provided are the titer comparisons of the anti-CD18 F(ab)'2-leucine zipper molecule derived from *E. coli* proteolytic mutants, with or without prc deletion. This data proved that 59A7 strain is a high producer of antibody expression. Various nucleic acids constructed for expressing anti-CD18 F(ab)'2-leucine zipper molecule are described; all the expression plasmids transformed into 59A7 strain produced higher amounts of antibody fragments when compared to a degPΔ single protease mutant or a degP prc mutant without spr. Another strain, 43H1, which has the genotype degP prc spr in addition to ompP and ptr3 mutations, did not grow as well as the 59A7 strain, although the 43H1 strain has the same spr mutation as that in 59A7, in that at position 520 it contains a change from T to C, resulting in a change from amino acid W to R at position 148. It produced anti-CD18 Fab'2 LZ with a titer higher than that produced by the degP strain (49A5), but not as high as that produced by the 59A7 strain in the fermentor.

The Prc protease was reported to cleave its substrates at a discrete number of sites but with rather broad sequence specificity (Keiler et al., supra). It has been found herein that the Prc cleavage sites in kappa-LC fragment are located in the constant region, which is the backbone sequence commonly used for constructing different humanized antibody expression plasmids. Based on the results herein, it is expected that the Prc deletion mutant would improve the titer of various antibody fragments, such as: Fab, Fab', and Fab'2 (with or without leucine zipper), and also of full-length antibody, expressed in *Escherichia coli* cells. The antibody fragment flanked with a His-tag or a Lys-tag sequence at the C-terminus of HC is also expected to benefit.

The strain 59A7 was found to be superior to strain 49A5 in expressing pAB3 and to be superior to strain 43E7 in specific expression of Apo2L cytoplasmic protein in shake flasks and superior to 43HI and 49A5 strains in expressing pS1130 and pcyc34 (the tacII promoter counterpart of pS1130) by fermentation. Further, it was superior to strain 33D3 in expressing the dual-promoter plasmid pxCD18-7T3.

EXAMPLE 2

Materials and Methods

A. Expression Plasmids

Plasmid D3H44-F(ab')2 is described in Example 1.
Plasmid pY0317tet20 is described in Example 1.

B. Strains

The strain used for xVEGF Fab expression is similar to other strains described in Example 1. It is a derivative of *E. coli* W3110 and is designated as 60C1. The complete genotype of 60C1 strain is W3110 ΔfhuA Δ(argF-lac) 169 ptr3 degP41 Kan$^s$ ΔompT ilvG2096(Val) Δ(nmpc-fepE) ΔssrA. Similar to 45F8 strain, it carries triple protease markers without prc.

Strains 43H1, 59A7, and 33B6 are all described in Example 1.

C. Culturing Method

Culturing in shake flasks was performed as described in Example 1. The growth of the shake-flask cultures expressing the xTF Fab'2 LZ-6xhis molecule was extended to 42 hours at 30° C., and two sets of samples were taken at different stages of growth for comparison. In the comparison of xVEGF Fab expression, duplicate cultures were grown, and only 24-hour time points were taken.

D. Protein Identification

The 2-D gel electrophoresis was conducted as described in Example 1.

Results

The data on the shake flask cultures are shown in Table 6 below. As is clear in Example 1 for rhuFab'2LZ (xCD18) production, the Prc− strains 43H1 and 59A7 were superior to the Prc+ strains 60C1 and 33B6 in the amounts of products produced (anti-VEGF Fab' and anti-tissue factor Fab'2 LZ-6xhis).

Figure 12:
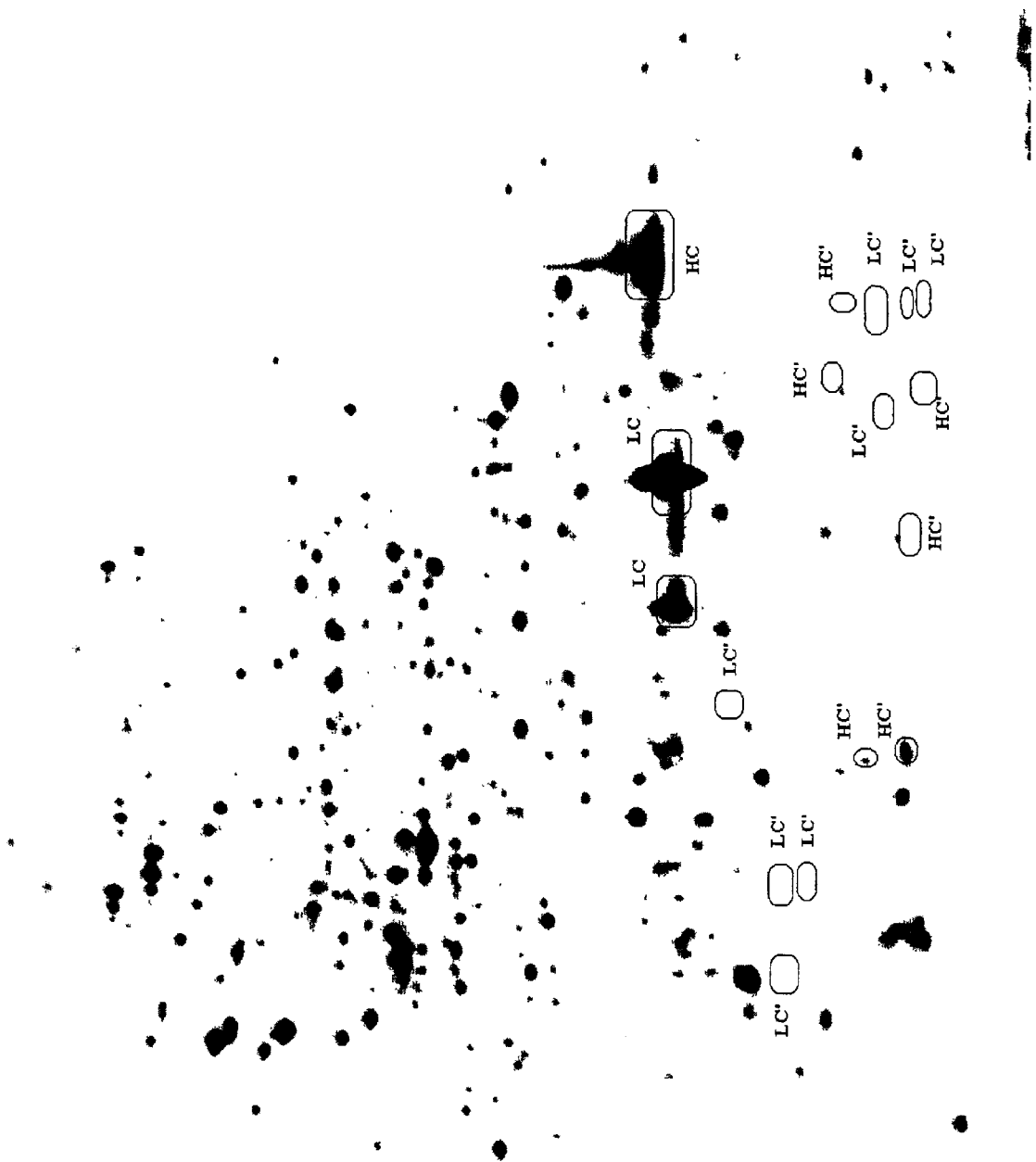
FIG. 12 depicts the 2-D gel result of the shake flask cell pellet derived from strain 59A7 (prc-minus strain) expressing the anti-VEGF Fab (pY0317tet20) as a heterologous polypeptide. In this gel the LC-cleavage products and two HC-cleavage fragments found in prc-plus cells disappear. Two separate HC clips detected in 59A7 only were also shown, which are either OmpT- or Ptr3-cleaved products.
Figure 13:
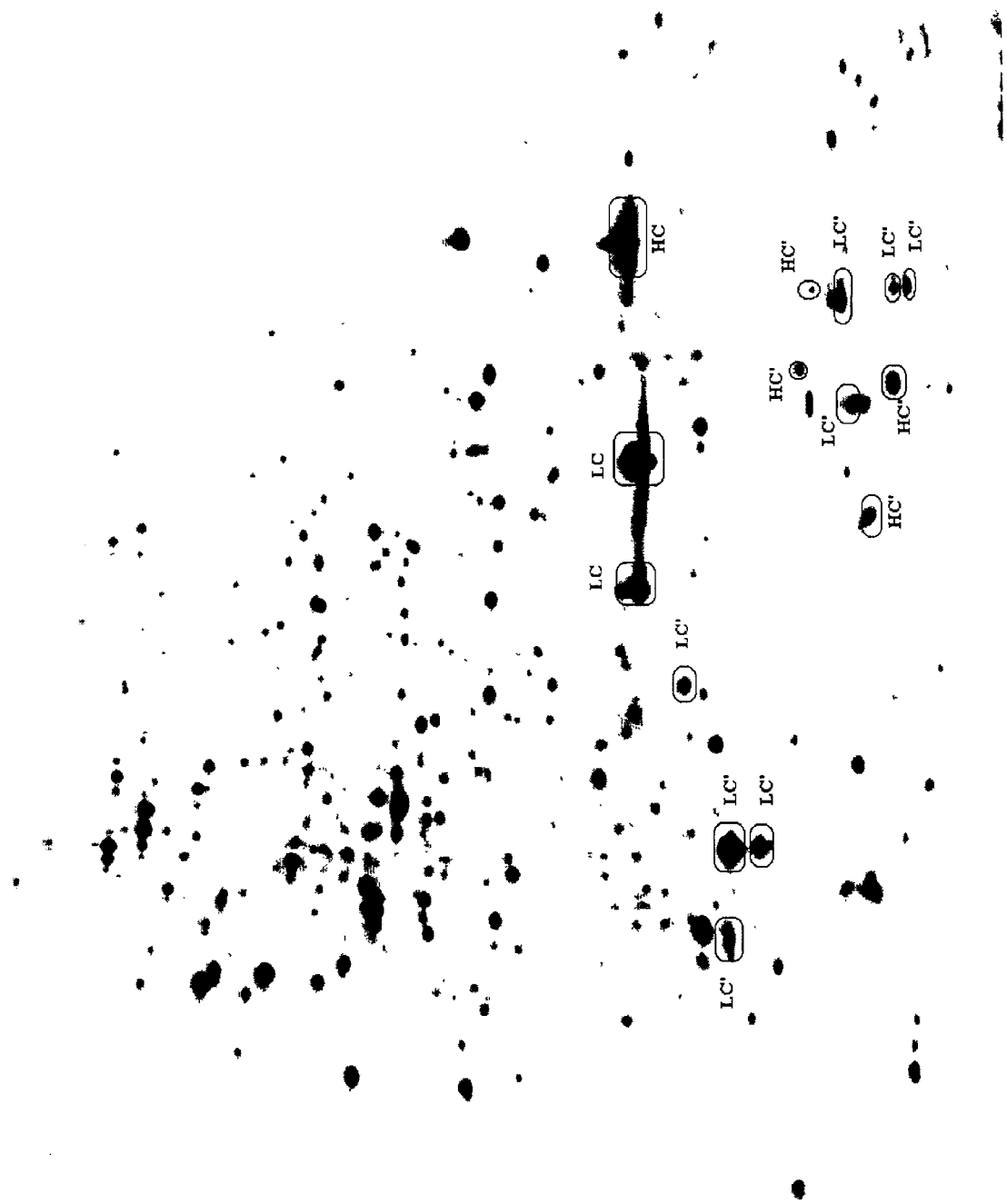
FIG. 13 depicts the 2-D gel result of the shake flask cell pellet derived from strain 60C1 (prc-plus strain) expressing the anti-VEGF Fab (pY0317tet20) as a heterologous polypeptide. In this gel, multiple LC-cleavage fragments and two HC-cleavage fragments were detected.

FIG. 12 is a 2-D gel showing that prc deletion (strain 59A7, the prc-minus strain) expressing the anti-VEGF Fab (pY0317tet20) eliminates all of the degraded anti-VEGF LC and two degraded xVEGF HC fragments (found in prc-plus strain), although two separate HC clips were discovered in 59A7, which are either OmpT- or Ptr3-cleaved products. FIG. 13 is a 2-D gel showing that the strain 60C1 (prc-plus strain) expressing the anti-VEGF Fab (pY0317tet20) as a heterologous polypeptide contained multiply degraded anti-VEGF LC and two degraded HC fragments.

TABLE 6

Shake Flask Data Comparing xVEGF Fab in prc+/− Host and xTF Fab'2 LZ-6x his Expression in prc+/− Host

| Strain | 24-hr. culture | 42-hr. culture | pst Status |
|---|---|---|---|
| | anti-VEGF Fab (mg/L/OD) | | |
| 59A7/pY0317tet20 | 2.44 | | − |
| 59A7/pY0317tet20 | 2.53 | | − |
| 60C1/pY0317tet20 | 0.82 | | + |
| 60C1/pY0317tet20 | 1.03 | | + |
| | anti-TF Fab'2 LZ-6xhis (mg/L/OD) | | |
| 33B6/pd3h44f2 | 0.68 | 0.54 | + |
| 43H1/pd3h44f2 | 1.60 | 1.88 | − |
| 59A7/pd3h44f2 | 2.18 | 3.98 | − |

What is claimed is:

1. An *E. coli* strain deficient in chromosomal degP and prc encoding protease DegP and Prc, respectively, and harboring a mutant spr gene, the product of which mutant spr gene comprises SEQ ID NO:12, wherein the tryptophan at position 148 is changed to arginin.

2. The strain of claim 1 that is not deficient in chromosomal ptr3 encoding Protease III or in chromosomal ompT encoding protease OmpT.

3. The strain of claim 1 comprising a nucleic acid encoding a polypeptide heterologous to the strain.

4. The strain of claim 3 wherein the polypeptide is proteolytically sensitive.

5. The strain of claim 3 wherein the polypeptide is a eukaryotic polypeptide.

6. The strain of claim 5 wherein the polypeptide is a mammalian polypeptide.

7. The strain of claim 3 that is transformed with the nucleic acid.

8. A method for producing a polypeptide comprising (a) culturing an *E. coli* strain deficient in chromosomal degP and prc encoding protease DegP and Prc, respectively, and harboring a mutant spr gene, the product of which mutant spr gene comprises SEQ ID NO:12, wherein the tryptophan at position 148 is changed to arginin, which strain comprises nucleic acid encoding the polypeptide, which is heterologous to the strain, such that the nucleic acid is expressed, and (b) recovering the heterologous polypeptide from the strain.

9. The method of claim 8 wherein the heterologous polypeptide is proteolytically sensitive.

10. The method of claim 8 wherein the culturing takes place in a fermentor.

11. The method of claim 10 wherein the culturing takes place under conditions of high-cell density fermentation.

12. The method of claim 10 wherein the culturing takes place under conditions of low-cell density fermentation.

13. The method of claim 8 wherein the polypeptide is recovered from the periplasm or culture medium of the strain.

14. The method of claim 8 wherein the polypeptide is an antibody or Apo2 ligand.

15. The method of claim 14 wherein the polypeptide is an antibody.

16. The method of claim 15 wherein the antibody is a humanized antibody.

17. The method of claim 15 wherein the antibody is a full-length antibody.

18. The method of claim 15 wherein the antibody is an anti-CD18, anti-VEGF, anti-tissue factor, 2C4, anti-Her-2, anti-CD20, anti-CD40, or anti-CD11a antibody.

19. The method of claim 15 wherein the antibody is an antibody fragment.

20. The method of claim 19 wherein the antibody fragment has a light chain.

21. The method of claim 20 wherein the light chain is a kappa light chain.

22. The method of claim 19 wherein the antibody fragment is a Fab, Fab', Fab'2, or Fab'2-leucine zipper fusion.

23. The method of claim 22 wherein the antibody fragment is anti-CD18 Fab'2-leucine zipper fusion, anti-tissue factor Fab'2-leucine zipper fusion, or anti-VEGF Fab, with or without a histidine or lysine tag.

24. The method of claim 22 wherein the antibody fragment is anti-CD18 Fab'2-leucine zipper fusion, anti-tissue factor Fab'2-leucine zipper fusion with a 6-histidine tag, anti-VEGF Fab, anti-CD18 Fab'2-leucine zipper fusion with a 6-histidine tag, or anti-CD18 Fab'2-leucine zipper fusion with a 6-lysine tag.

* * * * *

UNITED STATES PATENT AND TRADEMARK OFFICE
CERTIFICATE OF CORRECTION

PATENT NO. : 6,828,121 B2  
DATED : December 7, 2004  
INVENTOR(S) : Christina Yu-Ching Chen Page 1 of 1

It is certified that error appears in the above-identified patent and that said Letters Patent is hereby corrected as shown below:

Column 51,  
Lines 33 and 52, delete "arginin" and insert -- arginine --

Signed and Sealed this

Fifth Day of April, 2005

JON W. DUDAS  
*Director of the United States Patent and Trademark Office*

SEQUENCE LISTING

<160> NUMBER OF SEQ ID NOS: 12

<210> SEQ ID NO 1
<211> LENGTH: 1951
<212> TYPE: DNA
<213> ORGANISM: Artificial Sequence
<220> FEATURE:
<223> OTHER INFORMATION: Sequence is synthesized.

<400> SEQUENCE: 1

```
gaattcaact tctccatact ttggataagg aaatacagac atgaaaaatc         50
tcattgctga gttgttattt aagctttgga gattatcgtc actgcaatgc        100
ttcgcaatat ggcgcaaaat gaccaacagc ggttgattga tcaggtagag        150
```

-continued

| | |
|---|---|
| ggggcgctgt acgaggtaaa gcccgatgcc agcattcctg acgacgatac | 200 |
| ggagctgctg cgcgattacg taaagaagtt attgaagcat cctcgtcagt | 250 |
| aaaaagttaa tcttttcaac agctgtcata agttgtcac ggccgagact | 300 |
| tatagtcgct tgttttttat tttttaatgt atttgtaact agaattcgag | 350 |
| ctcggtaccc ggggatcctc tagaggttga ggtgatttta tgaaaaagaa | 400 |
| tatcgcattt cttcttgcat ctatgttcgt ttttctatt gctacaaacg | 450 |
| cgtacgctga tatccagttg acccagtccc cgagctccct gtccgcctct | 500 |
| gtgggcgata gggtcaccat cacctgcagc gcaagtcagg atattagcaa | 550 |
| ctatttaaac tggtatcaac agaaaccagg aaaagctccg aaactactga | 600 |
| tttacttcac ctcctctctc cactctggag tcccttctcg cttctctgga | 650 |
| tccggttctg ggacggatta cactctgacc atcagcagtc tgcagccaga | 700 |
| agacttcgca acttattact gtcaacagta tagcaccgtg ccgtggacgt | 750 |
| ttggacaggg taccaaggtg gagatcaaac gaactgtggc tgcaccatct | 800 |
| gtcttcatct tcccgccatc tgatgagcag ttgaaatctg gaactgcttc | 850 |
| tgttgtgtgc ctgctgaata acttctatcc cagagaggcc aaagtacagt | 900 |
| ggaaggtgga taacgccctc caatcgggta actcccagga gagtgtcaca | 950 |
| gagcaggaca gcaaggacag cacctacagc ctcagcagca ccctgacgct | 1000 |
| gagcaaagca gactacgaga aacacaaagt ctacgcctgc gaagtcaccc | 1050 |
| atcagggcct gagctcgccc gtcacaaaga gcttcaacag gggagagtgt | 1100 |
| taagctgatc ctctacgccg gacgcatcgt ggccctagta cgcaactagt | 1150 |
| cgtaaaaagg gtatctagag gttgaggtga ttttatgaaa agaatatcg | 1200 |
| catttcttct tgcatctatg ttcgtttttt ctattgctac aaacgcgtac | 1250 |
| gctgaggttc agctggtgga gtctggcggt ggcctggtgc agccaggggg | 1300 |
| ctcactccgt ttgtcctgtg cagcttctgg ctataccttc accaactatg | 1350 |
| gtatgaactg gatccgtcag gccccgggta agggcctgga atgggttgga | 1400 |
| tggattaaca cctataccgg tgaaccgacc tatgctgcgg atttcaaacg | 1450 |
| tcgttttact atatctgcag acacctccag caacacagtt tacctgcaga | 1500 |
| tgaacagcct gcgcgctgag gacactgccg tctattactg tgcaaagtac | 1550 |
| ccgcactatt atgggagcag ccactggtat ttcgacgtct ggggtcaagg | 1600 |
| aaccctggtc accgtctcct cggcctccac caagggccca tcggtcttcc | 1650 |
| ccctggcacc ctcctccaag agcacctctg ggggcacagc ggccctgggc | 1700 |
| tgcctggtca aggactactt ccccgaaccg gtgacggtgt cgtggaactc | 1750 |
| aggcgccctg accagcggcg tgcacacctt cccggctgtc ctacagtcct | 1800 |
| caggactcta ctccctcagc agcgtggtga ccgtgccctc cagcagcttg | 1850 |
| ggcacccaga cctacatctg caacgtgaat cacaagccca gcaacaccaa | 1900 |
| ggtcgacaag aaagttgagc ccaaatcttg tgacaaaact cacctctaga | 1950 |
| a | 1951 |

<210> SEQ ID NO 2
<211> LENGTH: 491
<212> TYPE: PRT

-continued

<213> ORGANISM: Artificial Sequence
<220> FEATURE:
<223> OTHER INFORMATION: Sequence is synthesized.

<400> SEQUENCE: 2

```
Met Lys Lys Asn Ile Ala Phe Leu Leu Ala Ser Met Phe Val Phe
 1               5                  10                  15

Ser Ile Ala Thr Asn Ala Tyr Ala Asp Ile Gln Leu Thr Gln Ser
                20                  25                  30

Pro Ser Ser Leu Ser Ala Ser Val Gly Asp Arg Val Thr Ile Thr
                35                  40                  45

Cys Ser Ala Ser Gln Asp Ile Ser Asn Tyr Leu Asn Trp Tyr Gln
                50                  55                  60

Gln Lys Pro Gly Lys Ala Pro Lys Leu Leu Ile Tyr Phe Thr Ser
                65                  70                  75

Ser Leu His Ser Gly Val Pro Ser Arg Phe Ser Gly Ser Gly Ser
                80                  85                  90

Gly Thr Asp Tyr Thr Leu Thr Ile Ser Ser Leu Gln Pro Glu Asp
                95                 100                 105

Phe Ala Thr Tyr Tyr Cys Gln Gln Tyr Ser Thr Val Pro Trp Thr
               110                 115                 120

Phe Gly Gln Gly Thr Lys Val Glu Ile Lys Arg Thr Val Ala Ala
               125                 130                 135

Pro Ser Val Phe Ile Phe Pro Pro Ser Asp Glu Gln Leu Lys Ser
               140                 145                 150

Gly Thr Ala Ser Val Val Cys Leu Leu Asn Asn Phe Tyr Pro Arg
               155                 160                 165

Glu Ala Lys Val Gln Trp Lys Val Asp Asn Ala Leu Gln Ser Gly
               170                 175                 180

Asn Ser Gln Glu Ser Val Thr Glu Gln Asp Ser Lys Asp Ser Thr
               185                 190                 195

Tyr Ser Leu Ser Ser Thr Leu Thr Leu Ser Lys Ala Asp Tyr Glu
               200                 205                 210

Lys His Lys Val Tyr Ala Cys Glu Val Thr His Gln Gly Leu Ser
               215                 220                 225

Ser Pro Val Thr Lys Ser Phe Asn Arg Gly Glu Cys Met Lys Lys
               230                 235                 240

Asn Ile Ala Phe Leu Leu Ala Ser Met Phe Val Phe Ser Ile Ala
               245                 250                 255

Thr Asn Ala Tyr Ala Glu Val Gln Leu Val Glu Ser Gly Gly Gly
               260                 265                 270

Leu Val Gln Pro Gly Gly Ser Leu Arg Leu Ser Cys Ala Ala Ser
               275                 280                 285

Gly Tyr Thr Phe Thr Asn Tyr Gly Met Asn Trp Ile Arg Gln Ala
               290                 295                 300

Pro Gly Lys Gly Leu Glu Trp Val Gly Trp Ile Asn Thr Tyr Thr
               305                 310                 315

Gly Glu Pro Thr Tyr Ala Ala Asp Phe Lys Arg Arg Phe Thr Ile
               320                 325                 330

Ser Ala Asp Thr Ser Asn Thr Val Tyr Leu Gln Met Asn Ser
               335                 340                 345

Leu Arg Ala Glu Asp Thr Ala Val Tyr Tyr Cys Ala Lys Tyr Pro
               350                 355                 360

His Tyr Tyr Gly Ser Ser His Trp Tyr Phe Asp Val Trp Gly Gln
```

```
                365                 370                 375
Gly Thr Leu Val Thr Val Ser Ser Ala Ser Thr Lys Gly Pro Ser
            380                 385                 390
Val Phe Pro Leu Ala Pro Ser Ser Lys Ser Thr Ser Gly Gly Thr
            395                 400                 405
Ala Ala Leu Gly Cys Leu Val Lys Asp Tyr Phe Pro Glu Pro Val
            410                 415                 420
Thr Val Ser Trp Asn Ser Gly Ala Leu Thr Ser Gly Val His Thr
            425                 430                 435
Phe Pro Ala Val Leu Gln Ser Ser Gly Leu Tyr Ser Leu Ser Ser
            440                 445                 450
Val Val Thr Val Pro Ser Ser Ser Leu Gly Thr Gln Thr Tyr Ile
            455                 460                 465
Cys Asn Val Asn His Lys Pro Ser Asn Thr Lys Val Asp Lys Lys
            470                 475                 480
Val Glu Pro Lys Ser Cys Asp Lys Thr His Leu
            485                 490

<210> SEQ ID NO 3
<211> LENGTH: 1042
<212> TYPE: DNA
<213> ORGANISM: Homo sapiens

<400> SEQUENCE: 3
tttcctcact gactataaaa gaatagagaa ggaagggctt cagtgaccgg            50
ctgcctggct gacttacagc agtcagactc tgacaggatc atggctatga           100
tggaggtcca ggggggaccc agcctgggac agacctgcgt gctgatcgtg           150
atcttcacag tgctcctgca gtctctctgt gtggctgtaa cttacgtgta           200
ctttaccaac gagctgaagc agatgcagga caagtactcc aaaagtggca           250
ttgcttgttt cttaaaagaa gatgacagtt attgggaccc caatgacgaa           300
gagagtatga cagcccctg ctggcaagtc aagtggcaac tccgtcagct            350
cgttagaaag atgattttga gaacctctga ggaaaccatt tctacagttc           400
aagaaaagca acaaaatatt tctcccctag tgagagaaag aggtcctcag           450
agagtagcag ctcacataac tgggaccaga ggaagaagca acacattgtc           500
ttctccaaac tccaagaatg aaaaggctct gggccgcaaa ataaaactcc           550 tgggaatcatc aaggagtggg cattcattcc tgagcaactt gcacttgagg          600
aatggtgaac tggtcatcca tgaaaaaggg ttttactaca tctattccca           650
aacatacttt cgatttcagg aggaaataaa agaaaacaca agaacgaca             700 aacaaatggt ccaatatatt tacaaataca caagttatcc tgaccctata           750
ttgttgatga aaagtgctag aaatagttgt tggtctaaag atgcagaata           800
tggactctat tccatctatc aagggggaat atttgagctt aaggaaaatg           850
acagaatttt tgtttctgta acaaatgagc acttgataga catggaccat           900
gaagccagtt ttttcggggc cttttagtt ggctaactga cctggaaaga            950
aaaagcaata acctcaaagt gactattcag ttttcaggat gatacactat          1000
gaagatgttt caaaaaatct gaccaaaaca aacaaacaga aa                  1042

<210> SEQ ID NO 4
<211> LENGTH: 281
```

```
<212> TYPE: PRT
<213> ORGANISM: Homo sapiens

<400> SEQUENCE: 4

Met Ala Met Met Glu Val Gln Gly Gly Pro Ser Leu Gly Gln Thr
  1               5                  10                  15

Cys Val Leu Ile Val Ile Phe Thr Val Leu Gln Ser Leu Cys
             20                  25                  30

Val Ala Val Thr Tyr Val Tyr Phe Thr Asn Glu Leu Lys Gln Met
             35                  40                  45

Gln Asp Lys Tyr Ser Lys Ser Gly Ile Ala Cys Phe Leu Lys Glu
             50                  55                  60

Asp Asp Ser Tyr Trp Asp Pro Asn Asp Glu Glu Ser Met Asn Ser
             65                  70                  75

Pro Cys Trp Gln Val Lys Trp Gln Leu Arg Gln Leu Val Arg Lys
             80                  85                  90

Met Ile Leu Arg Thr Ser Glu Glu Thr Ile Ser Thr Val Gln Glu
             95                 100                 105

Lys Gln Gln Asn Ile Ser Pro Leu Val Arg Glu Arg Gly Pro Gln
            110                 115                 120

Arg Val Ala Ala His Ile Thr Gly Thr Arg Gly Arg Ser Asn Thr
            125                 130                 135

Leu Ser Ser Pro Asn Ser Lys Asn Glu Lys Ala Leu Gly Arg Lys
            140                 145                 150

Ile Asn Ser Trp Glu Ser Ser Arg Ser Gly His Ser Phe Leu Ser
            155                 160                 165

Asn Leu His Leu Arg Asn Gly Glu Leu Val Ile His Glu Lys Gly
            170                 175                 180

Phe Tyr Tyr Ile Tyr Ser Gln Thr Tyr Phe Arg Phe Gln Glu Glu
            185                 190                 195

Ile Lys Glu Asn Thr Lys Asn Asp Lys Gln Met Val Gln Tyr Ile
            200                 205                 210

Tyr Lys Tyr Thr Ser Tyr Pro Asp Pro Ile Leu Leu Met Lys Ser
            215                 220                 225

Ala Arg Asn Ser Cys Trp Ser Lys Asp Ala Glu Tyr Gly Leu Tyr
            230                 235                 240

Ser Ile Tyr Gln Gly Gly Ile Phe Glu Leu Lys Glu Asn Asp Arg
            245                 250                 255

Ile Phe Val Ser Val Thr Asn Glu His Leu Ile Asp Met Asp His
            260                 265                 270

Glu Ala Ser Phe Phe Gly Ala Phe Leu Val Gly
            275                 280

<210> SEQ ID NO 5
<211> LENGTH: 212
<212> TYPE: PRT
<213> ORGANISM: Artificial Sequence
<220> FEATURE:
<223> OTHER INFORMATION: Sequence is synthesized.

<400> SEQUENCE: 5

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Ile Asn
             20                  25                  30

Asn Tyr Leu Asn Trp Tyr Gln Gln Lys Pro Gly Lys Ala Pro Lys
```

```
                35                  40                  45
Leu Leu Ile Tyr Tyr Thr Ser His Ser Gly Val Pro Ser Arg Phe
             50                  55                  60
Ser Gly Ser Gly Ser Gly Thr Asp Tyr Thr Leu Thr Ile Ser Ser
         65                  70                  75
Leu Gln Pro Glu Asp Phe Ala Thr Tyr Tyr Cys Gln Gln Gly Asn
             80                  85                  90
Thr Leu Pro Pro Thr Phe Gly Gln Gly Thr Lys Val Glu Ile Lys
             95                 100                 105
Arg Thr Val Ala Ala Pro Ser Val Phe Ile Phe Pro Pro Ser Asp
            110                 115                 120
Glu Gln Leu Lys Ser Gly Thr Ala Ser Val Val Cys Leu Leu Asn
            125                 130                 135
Asn Phe Tyr Pro Arg Glu Ala Lys Val Gln Trp Lys Val Asp Asn
            140                 145                 150
Ala Leu Gln Ser Gly Asn Ser Gln Glu Ser Val Thr Glu Gln Asp
            155                 160                 165
Ser Lys Asp Ser Thr Tyr Ser Leu Ser Ser Thr Leu Thr Leu Ser
            170                 175                 180
Lys Ala Asp Tyr Glu Lys His Lys Val Tyr Ala Cys Glu Val Thr
            185                 190                 195
His Gln Gly Leu Ser Ser Pro Val Thr Lys Ser Phe Asn Arg Gly
            200                 205                 210
Glu Cys

<210> SEQ ID NO 6
<211> LENGTH: 43
<212> TYPE: DNA
<213> ORGANISM: Artificial Sequence
<220> FEATURE:
<223> OTHER INFORMATION: Sequence is synthesized.

<400> SEQUENCE: 6
agcttgtcgg ggagcgccat caccatcacc atcactaagc atg          43

<210> SEQ ID NO 7
<211> LENGTH: 35
<212> TYPE: DNA
<213> ORGANISM: Artificial Sequence
<220> FEATURE:
<223> OTHER INFORMATION: Sequence is synthesized.

<400> SEQUENCE: 7
cttagtgatg gtgatggtga tggcgctccc cgaca              35

<210> SEQ ID NO 8
<211> LENGTH: 43
<212> TYPE: DNA
<213> ORGANISM: Artificial Sequence
<220> FEATURE:
<223> OTHER INFORMATION: Sequence is synthesized.

<400> SEQUENCE: 8
agcttgtcgg ggagcgcaaa aagaaaaaga aaaagtaagc atg          43

<210> SEQ ID NO 9
<211> LENGTH: 35
<212> TYPE: DNA
<213> ORGANISM: Artificial Sequence
<220> FEATURE:
```

<223> OTHER INFORMATION: Sequence is synthesized.

<400> SEQUENCE: 9 cttactttt cttttcttt ttgcgctccc cgaca 35

<210> SEQ ID NO 10
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 10

Cys Pro Pro Cys Pro Ala Pro Glu Leu Leu Gly Gly
 1               5                  10

<210> SEQ ID NO 11
<211> LENGTH: 188
<212> TYPE: PRT
<213> ORGANISM: Escherichia coli

<400> SEQUENCE: 11

Met Val Lys Ser Gln Pro Ile Leu Arg Tyr Ile Leu Arg Gly Ile
 1               5                  10                  15

Pro Ala Ile Ala Val Ala Val Leu Leu Ser Ala Cys Ser Ala Asn
                20                  25                  30

Asn Thr Ala Lys Asn Met His Pro Glu Thr Arg Ala Val Gly Ser
                35                  40                  45

Glu Thr Ser Ser Leu Gln Ala Ser Gln Asp Glu Phe Glu Asn Leu
                50                  55                  60

Val Arg Asn Val Asp Val Lys Ser Arg Ile Met Asp Gln Tyr Ala
                65                  70                  75

Asp Trp Lys Gly Val Arg Tyr Arg Leu Gly Gly Ser Thr Lys Lys
                80                  85                  90

Gly Ile Asp Cys Ser Gly Phe Val Gln Arg Thr Phe Arg Glu Gln
                95                  100                 105

Phe Gly Leu Glu Leu Pro Arg Ser Thr Tyr Glu Gln Gln Glu Met
                110                 115                 120

Gly Lys Ser Val Ser Arg Ser Asn Leu Arg Thr Gly Asp Leu Val
                125                 130                 135

Leu Phe Arg Ala Gly Ser Thr Gly Arg His Val Gly Ile Tyr Ile
                140                 145                 150

Gly Asn Asn Gln Phe Val His Ala Ser Thr Ser Ser Gly Val Ile
                155                 160                 165

Ile Ser Ser Met Asn Glu Pro Tyr Trp Lys Arg Tyr Asn Glu
                170                 175                 180

Ala Arg Arg Val Leu Ser Arg Ser
                185

<210> SEQ ID NO 12
<211> LENGTH: 162
<212> TYPE: PRT
<213> ORGANISM: Escherichia coli

<400> SEQUENCE: 12

Cys Ser Ala Asn Asn Thr Ala Lys Asn Met His Pro Glu Thr Arg
 1               5                  10                  15

Ala Val Gly Ser Glu Thr Ser Ser Leu Gln Ala Ser Gln Asp Glu
                20                  25                  30

-continued

```
Phe Glu Asn Leu Val Arg Asn Val Asp Val Lys Ser Arg Ile Met
                35                  40                  45

Asp Gln Tyr Ala Asp Trp Lys Gly Val Arg Tyr Arg Leu Gly Gly
                50                  55                  60

Ser Thr Lys Lys Gly Ile Asp Cys Ser Gly Phe Val Gln Arg Thr
                65                  70                  75

Phe Arg Glu Gln Phe Gly Leu Glu Leu Pro Arg Ser Thr Tyr Glu
                80                  85                  90

Gln Gln Glu Met Gly Lys Ser Val Ser Arg Ser Asn Leu Arg Thr
                95                 100                 105

Gly Asp Leu Val Leu Phe Arg Ala Gly Ser Thr Gly Arg His Val
               110                 115                 120

Gly Ile Tyr Ile Gly Asn Asn Gln Phe Val His Ala Ser Thr Ser
               125                 130                 135

Ser Gly Val Ile Ile Ser Ser Met Asn Glu Pro Tyr Trp Lys Lys
               140                 145                 150

Arg Tyr Asn Glu Ala Arg Arg Val Leu Ser Arg Ser
               155                 160
```